ID 
US011185580B2

(12) United States Patent
Garcea et al.

(10) Patent No.: US 11,185,580 B2
(45) Date of Patent: Nov. 30, 2021

(54) COMPOSITIONS, METHODS AND USES FOR IMPROVED HUMAN PAPILLOMA VIRUS CONSTRUCTS

(71) Applicant: The Regents of the University of Colorado, a body corporate, Denver, CO (US)

(72) Inventors: Robert L. Garcea, Boulder, CO (US); Dennis G. Macejak, Arvada, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 29 days.

(21) Appl. No.: 16/530,786

(22) Filed: Aug. 2, 2019

(65) Prior Publication Data
US 2020/0121779 A1    Apr. 23, 2020

Related U.S. Application Data

(63) Continuation of application No. 15/320,277, filed as application No. PCT/US2015/036753 on Jun. 19, 2015, now Pat. No. 10,413,603.

(60) Provisional application No. 62/014,495, filed on Jun. 19, 2014.

(51) Int. Cl.
| | |
|---|---|
| A61K 39/12 | (2006.01) |
| C12N 15/70 | (2006.01) |
| C07K 14/005 | (2006.01) |
| C12N 7/00 | (2006.01) |
| A61K 39/00 | (2006.01) |

(52) U.S. Cl.
CPC ............ *A61K 39/12* (2013.01); *C07K 14/005* (2013.01); *C12N 7/00* (2013.01); *C12N 15/70* (2013.01); *A61K 2039/53* (2013.01); *C12N 2710/20022* (2013.01); *C12N 2710/20034* (2013.01); *C12N 2800/101* (2013.01); *C12N 2800/22* (2013.01)

(58) Field of Classification Search
CPC combination set(s) only.
See application file for complete search history.

(56) References Cited

U.S. PATENT DOCUMENTS

| | | | |
|---|---|---|---|
| 6,165,471 A | 12/2000 | Garcea et al. | |
| 6,228,368 B1* | 5/2001 | Gissmann | A61P 35/00 424/204.1 |
| 7,371,391 B2* | 5/2008 | Gissmann | C12N 7/00 424/204.1 |
| 7,754,430 B2* | 7/2010 | Gissmann | A61P 31/12 435/5 |

FOREIGN PATENT DOCUMENTS

EP    2377879 A1    10/2011

OTHER PUBLICATIONS

De Boer et al. Proc. Natl. Acad, Sci. USA, 1983, vol. 80, pp. 21-25.*
Tomita et al. Journal of Virology, 1987, vol. 61, No. 8, pp. 2389-2394.*
Kelsall S et al. Journal of Virological Methods, 1995, vol. 53, pp. 75-90.*
Sun, "Application of insect cell expression of prophylactic human papillomavirus vaccine and application of packed bed bioreactor to express H1N1 influenza virus vaccine", Chinese Doctoral dissertations, Medicine and Health Sciences, 2013, 16 pages (Chinese only).
Ma et al., "Increasing the expression levels of papillomavirus major capsid protein in *Escherichia coli* by n-terminal deletion", 2007, vol. 56, No. 1, pp. 72-79.
Sun, "Application of insect cell expression of prophylactic human papillomavirus vaccine and application of packed bed bioreactor to express H1N1 influenza virus vaccine", Chinese Doctoral dissertations, Medicine and Health Sciences, 2013, along with English translation summary, 18 pages.
Chen et al., "Papillomavirus Capsid Protein Expression in *Escherichia coli*: Purification and Assembly of HPV11 and HPV16 L1", J. Mol. Biol., 2001, vol. 307, pp. 173-182.
Kimbauer et al., "Efficient Self-Assembly of Human Papillomavirus Type 16 L1 and L1-L2 in Virus-Like Particles," Journal of Virology, 1993, vol. 67, No. 12, jpp. 6929-6939.
Kimbauer et al., "Papillomavirus L1 major capsid protein self-assembles into virus-like particles that are highly immunogenic," Proc. Natl. Aca. Sci. USA, 1992, vol. 89, pp. 12190-12184.
Kim et al., "Enhanced immunogenicity of human papillomavirus 16 L1 genetic vaccines fused to an ER-targeting secretory signal peptide and RANTES," Gene Therapy, 2003, vol. 10, pp. 1268-1273.
Wu et al., "Capsomer Vaccines Protect Mice from Vaginal Challenge with Human Papillomavirus," PLoS ONE, 2011, vol. 6, No. 11, 8 pages.

* cited by examiner

*Primary Examiner* — Bao Q Li
(74) *Attorney, Agent, or Firm* — Polsinelli PC

(57) ABSTRACT

Embodiments of the present invention provide compositions and methods for recombinantly generating tagless constructs of proteins or peptides. In certain embodiments, recombinant proteins or peptides disclosed herein concern human papilloma virus (HPV). Other embodiments concern using these constructs in compositions to elicit immune responses in a subject to one or more HPV types. Therapeutic and prophylactic vaccines for the prevention and treatment of viral infections are also disclosed. Nucleic acids and expression vectors coding for constructs contemplated herein are provided. In certain embodiments, an HPV capsid protein generated is devoid of any fusion tags. In addition, truncated forms of HPV L1 are contemplated.

21 Claims, 14 Drawing Sheets
Specification includes a Sequence Listing.

L - 1KB DNA Ladder (Biotium #31021)
1 - HPV16-p3 #1 clone
2 - HPV16-p3 #2 clone (after 3rd selection)
3 - HPV16-p3 #3 clone (after 3rd selection)
4 - HPV16-p3 #4 clone (after 3rd selection)

- Transformed and purified 3X in Terrific Broth
- HPV16-p3 plasmid restriction digestion with XhoI and NdeI. (insert ~1500bp)
- 3 clones with the 3rd clone selection.
- Gel: 1%TBE

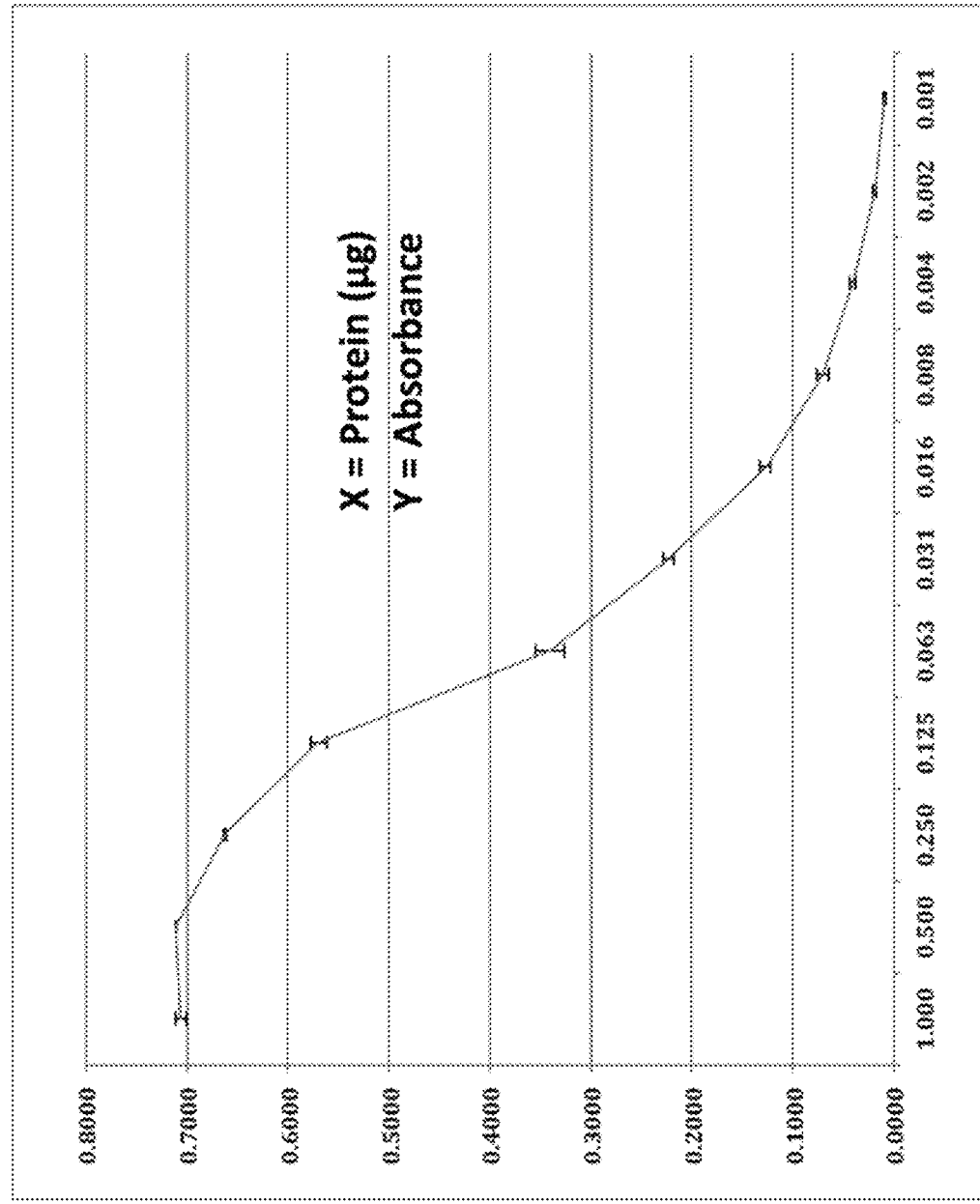
Fig. 4: V5 Conformational Antibody ELISA

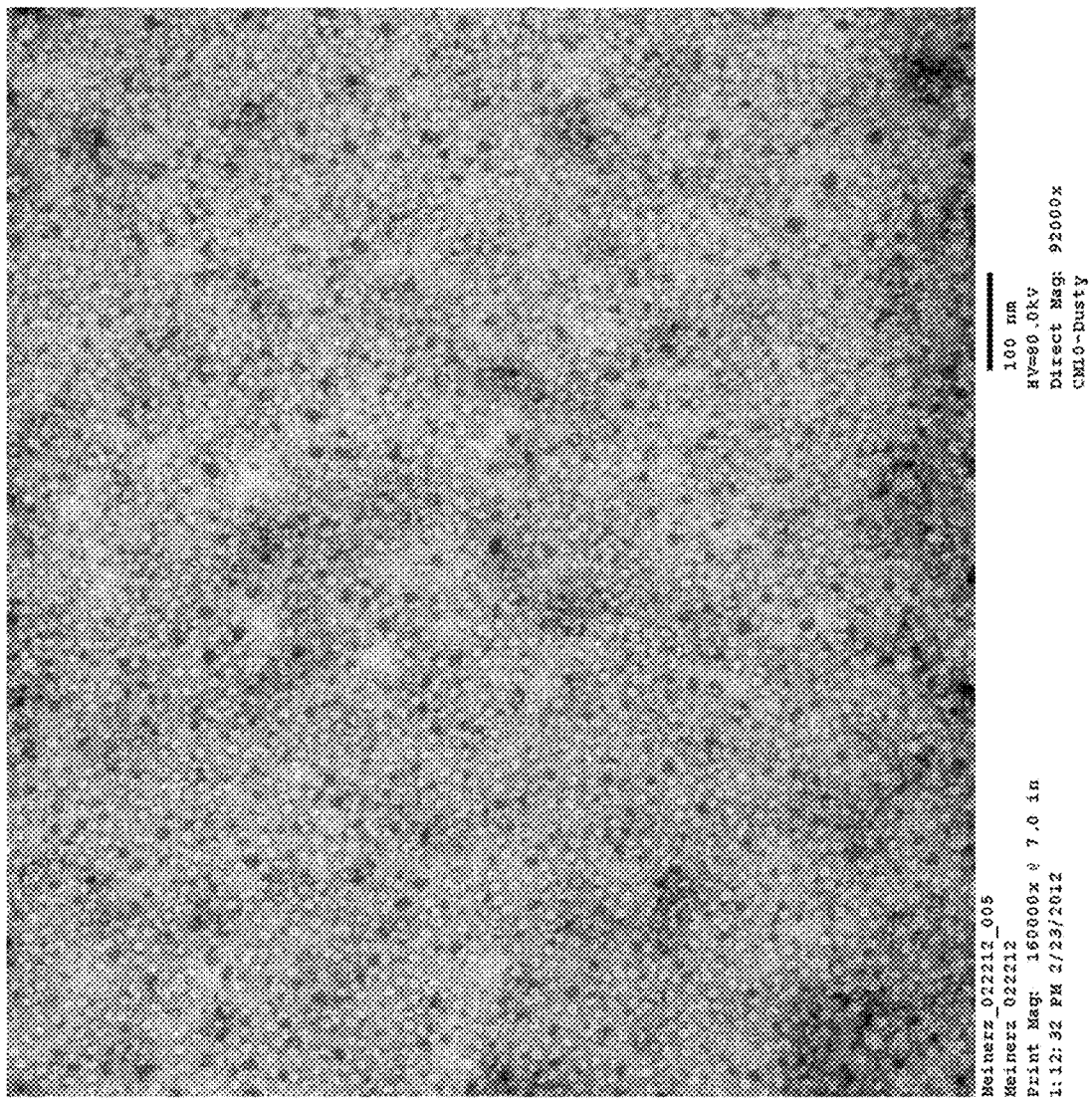
Fig. 5: Electron Microscopy Visualization of Pentamers

PsV16 Neutralization Assay

PsV18 Neutralization Assay

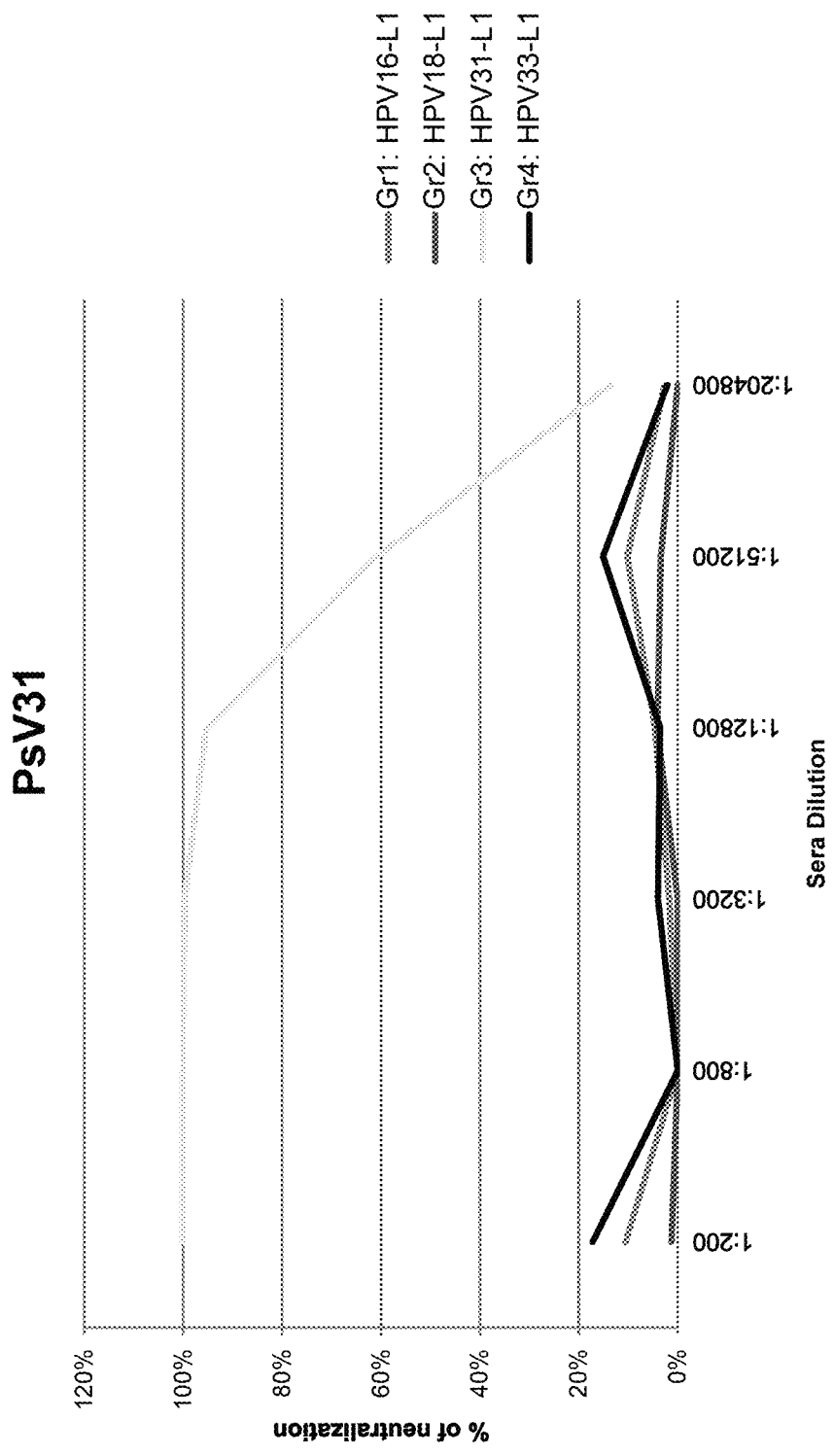

Figs. 7A - 7C  HPV16L1 ΔN3, ΔN5 & ΔN9
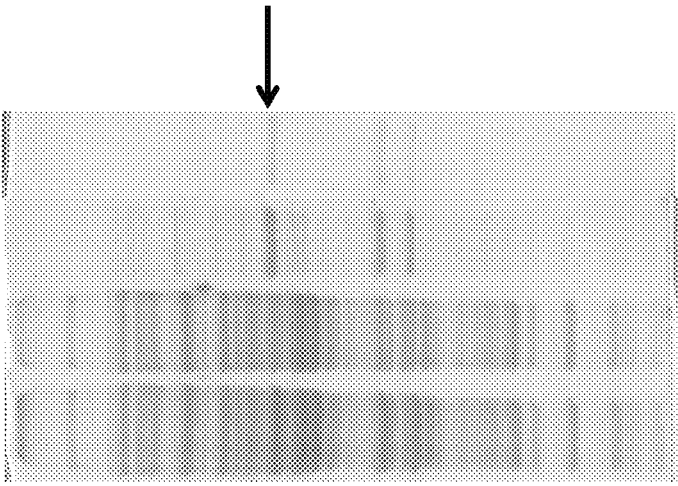
Fig. 7A  ΔN3
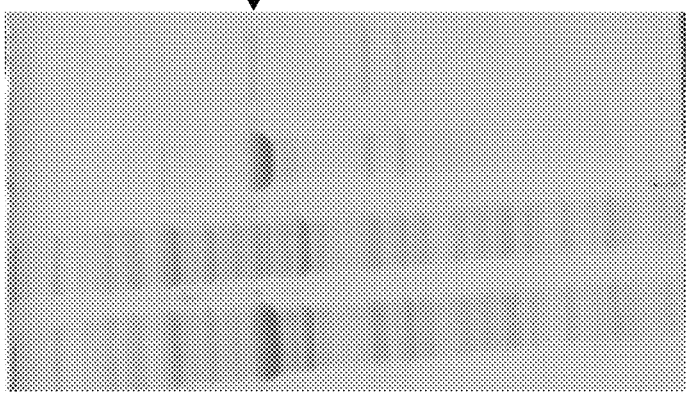
Fig. 7B  ΔN5
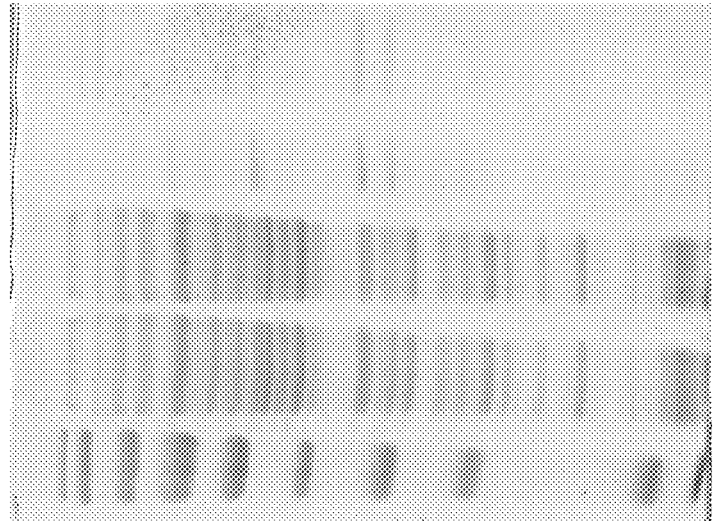
Fig. 7C  ΔN9

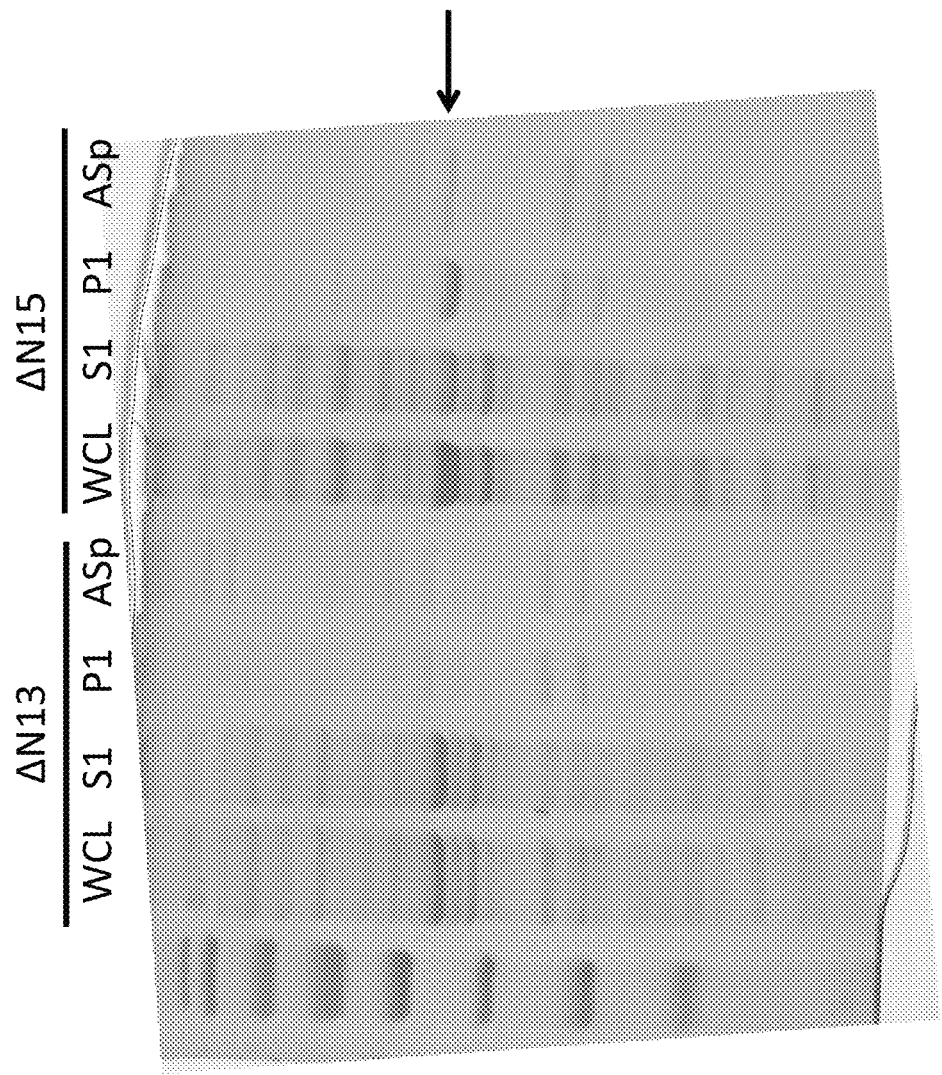
Fig. 8 HPV16L1 ΔN13 & ΔN15

HPV16L1 ΔN20 & ΔN25

HPV18L1 ΔN5 & ΔN9

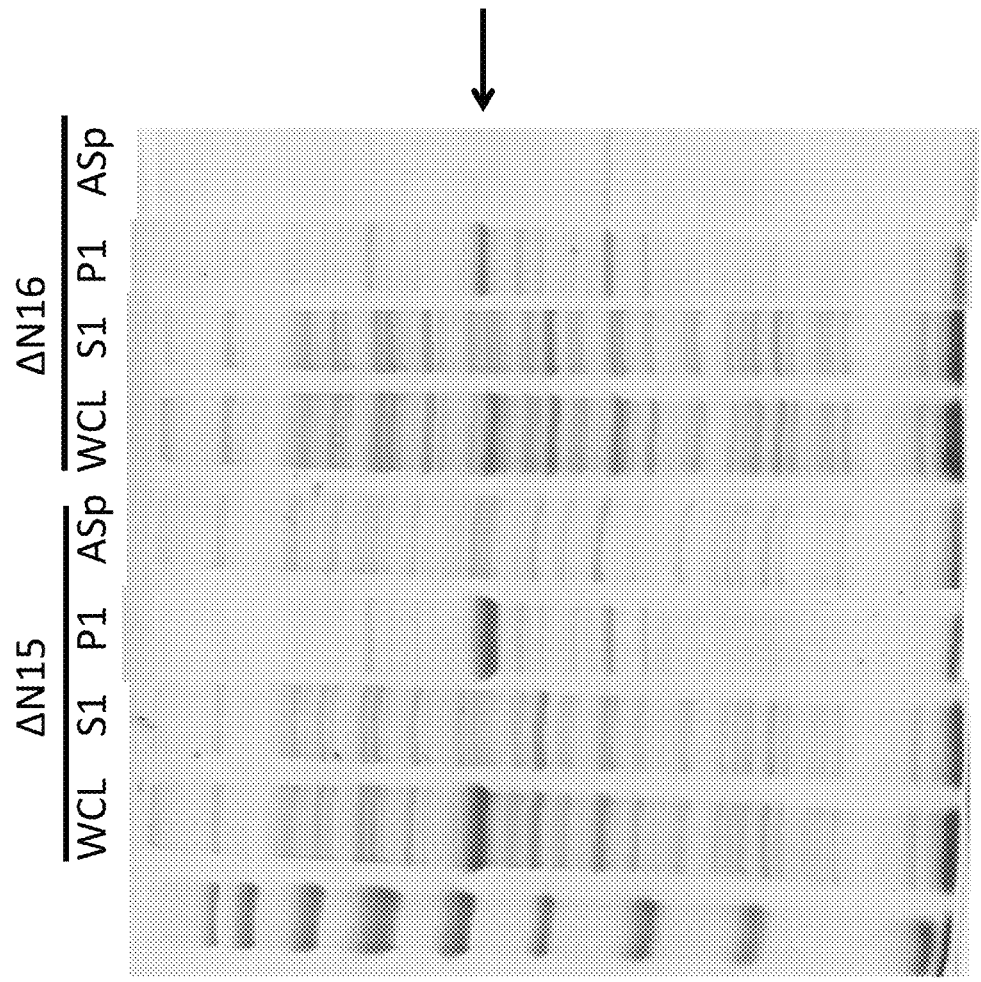
Fig.11 HPV18L1 ΔN15 & ΔN16

COMPOSITIONS, METHODS AND USES FOR IMPROVED HUMAN PAPILLOMA VIRUS CONSTRUCTS

PRIORITY

This Continuation Application claims priority to U.S. Non-Provisional application Ser. No. 15/320,277 filed Dec. 19, 2016, issued Sep. 17, 2019 as U.S. Pat. No. 10,413,603 and PCT Application No. PCT/US2015/036753 filed Jun. 19, 2015 which claims priority to U.S. Provisional Application No. 62/014,495 filed Jun. 19, 2014. These applications are incorporated herein in their entirety by reference for all purposes.

The instant application contains a Sequence Listing which has been submitted via EFS-Web and is hereby incorporated by reference in its entirety.

GOVERNMENT FUNDING

This invention was made with government support under grant number CA098252 awarded by the National Institutes of Health. The government has certain rights in the invention.

FIELD OF THE INVENTION

Embodiments of the present invention provide novel vaccines and diagnostic agents for the prevention, treatment and/or diagnosis of human papilloma virus infection and cervical cancers associated therewith. Some embodiments herein concern human papillomavirus (HPV) constructs devoid of a tag, tracking agent or fusion element. These preparations can then be used to elicit immune responses in a subject to target HPVs. In certain embodiments, the HPV constructs generated by compositions and methods disclosed herein are capsomeres.

BACKGROUND OF THE INVENTION

Papillomaviruses are pathogenic viruses that can infect a wide variety of different species of animals that include humans. Papillomavirus infection is often characterized by the induction of epithelial and fibro-epithelial tumors, or warts at the site of infection. Each species of vertebrate is infected by a species-specific set of Papillomavirus. For example, more than one hundred different human papillomavirus (HPV) genotypes have been isolated to date. Papillomaviruses are highly species-specific infective agents. Canine and rabbit papillomaviruses are not known to induce papillomas in heterologous species such as humans. Immunity to infection against one papillomavirus type generally does not appear to confer immunity against another type, even when the types infect a homologous species.

Papillomaviruses cause genital warts, a prevalent sexually-transmitted disease in humans. HPV types 6 and 11 are most commonly associated with benign genital warts condylomata acuminata. Genital warts are very common, and subclinical or unapparent HPV infection is even more common than clinical infection. While most HPV-induced lesions are benign, lesions arising from certain papillomavirus types (e.g., HPV-16 and HPV-18) can undergo malignant progression to potentially lead to cervical cancer. Of the HPV genotypes involved in cervical cancer, HPV-16 is the most common, being found in about 50% of cervical cancers.

In view of the significant health risks posed by papillomavirus infection generally, and human papillomavirus infection in particular, various groups have reported the development of recombinant papillomavirus antigens and their use as diagnostic agents and as prophylactic vaccines. In general, such research has been focused toward producing prophylactic vaccines containing the major capsid protein (L1) alone or in combination with the minor capsid protein (L2).

Prophylactic vaccines currently in clinical trials are based upon VLPs (virus-like particles). VLPs are assemblies of 72 pentamers or capsomeres of the major papillomavirus capsid protein L1. However, these types of vaccines are relatively expensive to produce in that they require eukaryotic expression systems or complex purification, and are less stable than capsomere preparations. VLP vaccines may not provide cross protection against other papillomavirus serotypes, as neutralizing immune responses tend to be predominately type-specific.

SUMMARY OF THE INVENTION

Embodiments disclosed herein provide efficient compositions and methods for production of human papilloma virus (HPV) capsomeres, subunits of the virus capsid, devoid of affinity or other tags wherein the constructs are tagless. In accordance with these embodiments, the HPV capsomeres can be generated using compositions and methods disclosed herein from any HPV species.

In other embodiments, HPV proteins or peptides generated herein can be used to generate capsomeres of use in immunogenic compositions described. In accordance with these embodiments, capsomeres of embodiments disclosed herein can be used to cost effectively, efficiently and readily produce an immunogenic composition for immunizing a subject in order to reduce the risk of onset or developing an HPV infection or treating a subject having an HPV infection.

Some embodiments concern using HPV-protein producing constructs to generate large amounts of proteins compared to standard methods while eliminating the need to remove a tag or fusion molecule making the process more efficient. These tagless constructs can be used to form capsomeres of use in immunogenic compositions disclosed herein. Certain immunogenic compositions contemplated herein can be pharmaceutically acceptable compositions that are immunogenic compositions of use to generate vaccines or other compositions of use to immunize a subject against a papilloma infection. These compositions can be used to elicit immune responses in a subject to a human papillomavirus in order to protect the subject from HPV infection. Prophylactic vaccines for the prevention and/or treatment of viral infection, such as papillomavirus infection, cervical cancers and warts associated therewith, generated from compositions disclosed herein are described. Nucleic acids and expression vectors encoding papilloma virus constructs or polypeptides of use in compositions are also disclosed.

In some embodiments, constructs generated by methods disclosed herein can be used to express HPV polypeptides in a bacterial expression system for rapid and cost effective generation and purification of large quantities of HPV polypeptides. In accordance with these embodiments, HPV polypeptides produced by these methods can be of use in pharmaceutical compositions or other compositions. Further processing is not required because these HPV polypeptides are not fused to or does not include a tag or other tracking molecule.

Other embodiments further provide capsomere formulations generated using the tagless constructs described herein. For example, intact structural papilloma viral protein L1 can be used to generate tagless constructs. The sequence of L1 is well known in the art and can be found for example, in U.S. Pat. No. 6,228,368 that is incorporated herein in its entirety. Certain embodiments concern truncated forms of HPV L1. In accordance with these embodiments, a truncated form of HPV L1 described herein can include one that has a truncation of at least 3 but no more than 24 amino acids positioned at the N-terminus and up to 29 amino acids at the C-terminus. In accordance with these embodiments, truncated L1 proteins can form a pentameric capsomere subunit and can contain a neutralizing epitope found in HPV virions, but is deficient in the ability to form higher-ordered structures such as the complete virus capsid or VLPs.

BRIEF DESCRIPTION OF THE FIGURES

The following drawings form part of the present specification and are included to further demonstrate certain embodiments. Some embodiments may be better understood by reference to one or more of these drawings alone or in combination with the detailed description of some embodiments presented.

FIG. 4 represents ELISA reactivity with V5 conformational antibody.

FIG. 5 represents an electron micrograph confirming characteristic pentamer formation.

FIG. 6A-6D represent graphs from HPV pseudovirus neutralization assays, 6A represents PsV16; 6B represents PsV18, 6C represents PsV31 and 6D represents PsV33.

FIGS. 7A-7C represents an image of a representative SDS-PAGE demonstrating expression of HPV16L1 with N-terminal deletions of 3 (7A), 5 (7B) or 9 (7C) amino acids.

FIG. 8 represents an image of a representative SDS-PAGE demonstrating expression of HPV16L1 with N-terminal deletions of 13 or 15 amino acids.

FIG. 11 represents an image of a representative SDS-PAGE demonstrating expression of HPV18L1 with N-terminal deletions of 15 or 16 amino acids.

DETAILED DESCRIPTION OF THE INVENTION

Figure 1:
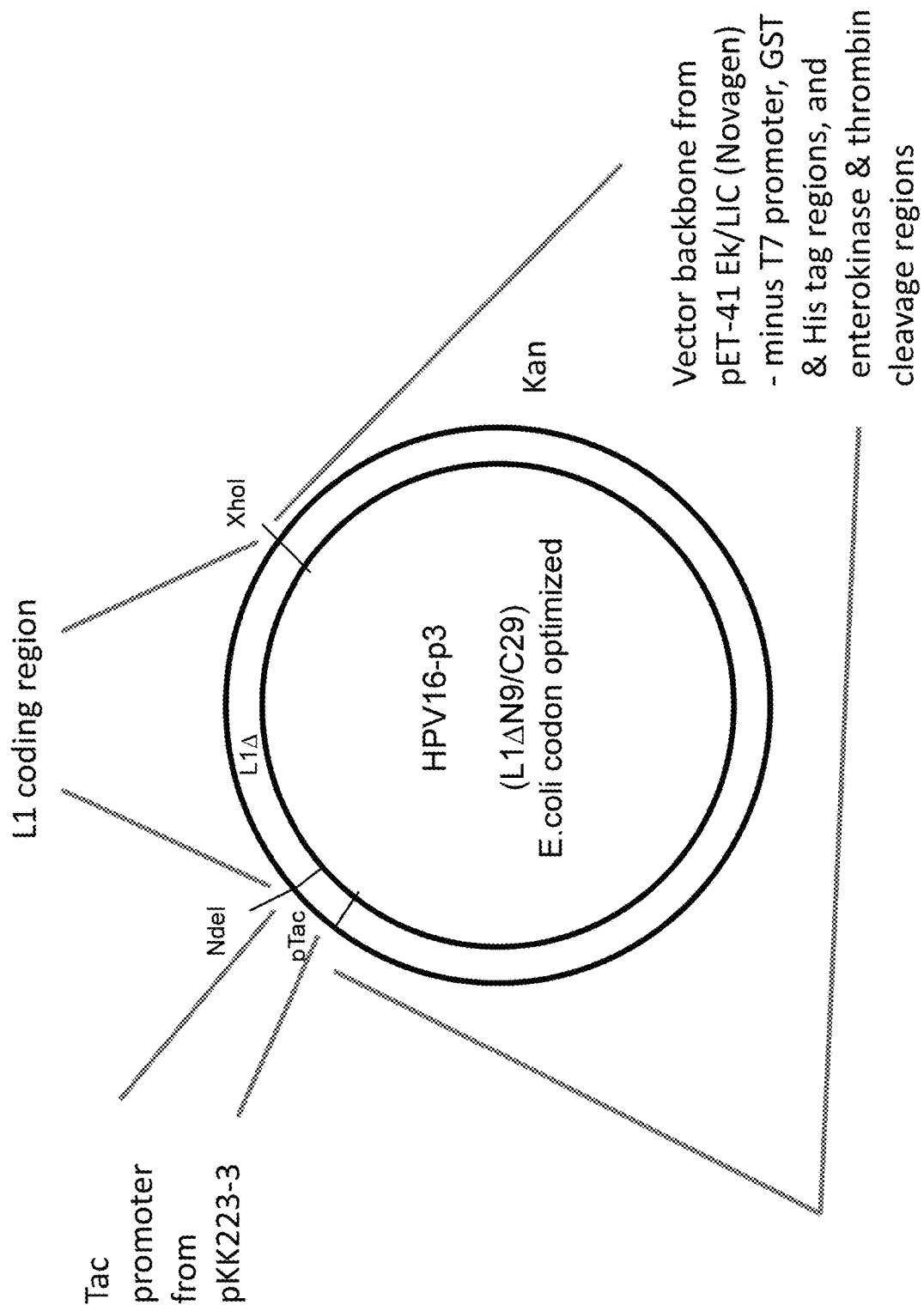
FIG. 1 illustrates an exemplary expression plasmid construct of certain embodiments disclosed herein.

In the following sections, various exemplary compositions and methods are described in order to detail various embodiments. It will be obvious to one skilled in the art that practicing the various embodiments does not require the employment of all or even some of the details outlined herein, but rather that concentrations, times and other details may be modified through routine experimentation. In some cases, well-known methods or components have not been included in the description.

Compositions and methods disclosed herein relate to efficiently and cheaply producing large quantities of target proteins or peptides wherein production of the target utilizes no tag or fusion polypeptide for production or isolation. It is contemplated that these methods are effective for quickly producing a target protein avoiding the unnecessary steps involved with utilizing a tag or other tracking agent.

It was previously described that papillomavirus capsid protein L1 proteins can be expressed from a construct as a fusion protein. These fusion proteins as expressed in bacterial organisms as recombinant molecules can retain L1 native conformation and immunogenic activity as measured by assays with for example, neutralizing antibodies. Current protein or peptide constructs known in the art require tags for expression in order to follow synthesis and/or purification of a target protein or peptide leading to extra expenses in materials (e.g. tag or tracking agents) and labor to remove the tag from the final products in preparation for storage and subsequent use. These additional requirements slow down the process for production and in certain cases can make manufacturing of the target molecule cost prohibitive. Enclosed herein disclose compositions and methods to overcome these issues and rapidly produce large quantities of cost effective useful protein products. Thus, a protein or peptide of interest can be manufactured rapidly and at a significantly reduced cost.

In certain embodiments, compositions and methods herein concern producing human papilloma virus (HPV) proteins or peptides of use in compositions disclosed for the manufacture of these peptides or proteins as well as use thereof in the manufacture of vaccines. In certain embodiments, a protein contemplated herein can be a capsid protein. A capsid protein is a structural protein of a virus. Capsid proteins are typically described by whether they are the predominant (major) or lesser (minor) constituent of capsid structure. The major constituent of the papillomavirus (PV) capsid structure is capsid protein L1 protein. HPV L1 DNA may be derived from any strain of HPV, such as from an HPV that is involved in causing cancer or other health condition. HPV L1 may be derived from one or more of the following strains, including, but not limited to, HPV-16, HPV-18, HPV-31, HPV-33, HPV-35, HPV-39, HPV-45, HPV-51, HPV-52, HPV-56, and HPV-58 associated with cancer, and HPV-6, HPV-11, HPV-30, HPV-42, HPV-43, HPV-44, HPV-54, HPV-55, and HPV-70, associated with warts.

In certain embodiments, proteins or peptides generated by compositions and methods disclosed herein include correctly-folded L1 protein: or fragment thereof, or mutated form thereof. In accordance with these embodiments, the protein or peptide assumes a conformational structure that presents one or more HPV L1 epitopes. These epitopes are present on native viral capsids or VLPs. In some embodiments, a correctly folded HPV L1 protein can represent one or more HPV L1 conformational epitopes. Presentation of conformational epitopes appears to be essential to the efficacy (both as prophylactic and diagnostic agents) of HPV L1 protein immunogens.

In other embodiments, HPV L1 proteins can be generated to rapidly produce capsomeres made up of the L1 proteins. A capsomere is a subunit structure that makes up the larger viral capsid structure. A native HPV capsomere consists of a pentamer of L1 capsid proteins and a monomer of the minor capsid protein, L2. However, a capsomere containing only the L1 pentamer is sufficient to induce neutralizing antibodies. In some embodiments, an L1 and L2 combination may be produced while in others only L1 may be produced for use in the manufacture of capsomere compositions.

In other embodiments, constructs contemplated herein can be used to generate L1 proteins or peptides of use in vaccine formulations. In accordance with these embodiments, these constructs can include capsomeres of full-length or truncated L1. Truncated proteins contemplated herein include those having one or more amino acid residues deleted from the carboxy-terminus of the protein, one or more amino acid residues deleted from the amino terminus of the protein, one or more amino acid residues deleted from an internal region (e.g., not from either terminus) of the protein, or a combination of such deletions. In addition, a truncated form of HPV L1 described herein can include one that has a truncation of at least 3 but no more than 24 amino acids positioned at the N-terminus and up to 29 amino acids at the C-terminus. In accordance with these embodiments, truncated L1 proteins can form a pentameric capsomere subunit and can contain a neutralizing epitope found in HPV virions, but is deficient in the ability to form higher-ordered structures such as the complete virus capsid or VLPs.

In addition this invention includes proteins having specific cysteine mutations that prevent assembly into VLPs. It is contemplated that any protein or peptide derived from L1 can contain a methionine as the first amino acid and that when expressed forms at least one conformational, neutralizing epitope of use herein.

In the case of polypeptide sequences that are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine. Similar minor variations may also include amino acid deletions or insertions, or both. Guidance in determining which amino acid residues may be substituted, inserted, or deleted without abolishing biological or immunological activity may be found using computer programs well known in the art.

Viral proteins of the present invention may be derived from any papillomaviruses. In certain embodiments, viral proteins are any human papillomavirus. Many HPV L1 DNAs have been reported in the literature and are publicly available. (See, e.g., Baker, Sequence Analysis of Papillomavirus, Genomes, pp. 321-384; Long, et al., U.S. Pat. No. 5,437,931; Cole, et al., J Mol. Biol., 193:599-608 (1987); Danos, et al., EMBO J, 1:231-236 (1982); Cole, et al., J Virol., 38(3):991-995 (1986)). Any of these disclosed HPV L1 DNAs are of use in methods and compositions disclosed herein. Numerous HPV L1 DNAs have been cloned and expressed and are available for use in constructs as described in certain embodiments disclosed.

Some embodiments herein relate to producing target proteins and polypeptides using expression systems such as a prokaryotic or other appropriate host systems. In accordance with these embodiments, a prokaryotic host cell can include bacteria such as E. coli or other microorganisms. It is also contemplated that eukaryotic host cells can be used. Any of the host cells contemplated of use to produce the target molecules of interest can be cultured under conditions that favor the production of capsid proteins. This can depend upon the selected host system and regulatory sequences contained in the vector, e.g., whether expression of the capsid protein requires induction. Target proteins and polypeptides may also be expressed in any host cell that provides for the expression of recoverable yields of the polypeptides in appropriate conformation. Suitable host systems for expression of recombinant proteins are well known and include, but are not limited to, bacteria, mammalian cells, yeast, and insect cells. In one embodiment, an expression system can include an E. coli expression system because these systems are known to produce high capsomere yields.

Suitable vectors for cloning and expressing polypeptides of the present invention are well known in the art and commercially available. Further, suitable regulatory sequences for achieving cloning and expression, e.g., promoters, polyadenylation sequences, enhancers and selectable markers are also well known. In certain embodiments, a modified vector can include a vector composed of HPV DNA, a promoter for expression of the HPV DNA, a resistance gene (e.g. kanamycin resistance) and additional filler sequences.

For expression in an appropriate expression system, an L1 nucleic acid encoding a polypeptide is operably linked into an expression vector and introduced into a host cell to enable the expression of the L1 protein by that cell. The gene with the appropriate regulatory regions will be provided in the proper orientation and reading frame to allow for expression. Methods for gene construction are known in the art.

It will be appreciated by those skilled in the art that as a result of the degeneracy of the genetic code, a multitude of nucleotide sequences encoding chimeric proteins and complexes/capsomeres, some bearing minimal homology to the nucleotide sequences of any known and naturally occurring gene, may be produced. Thus, it is contemplated that each and every possible variation of nucleotide sequence that could be made by selecting combinations based on possible codon choices can be generated. These combinations can be made in accordance with the standard triplet genetic code as applied to the nucleotide sequence of naturally occurring chimeric proteins and complexes/capsomeres of the present invention, and all such variations are to be considered as being specifically disclosed.

It may be advantageous to produce nucleotide sequences encoding proteins and capsomeres possessing a substantially different codon usage. Codons may be selected to increase the rate at which expression of the peptide occurs in a particular prokaryotic or eukaryotic host in accordance with the frequency with which particular codons are utilized by the host.

Some embodiments concern using proteins, polypeptides and capsomeres produced herein for both prophylactic administration to reduce the risk of infection, for treatment of an infections and for diagnostics of an existing condition. Suitability of the proteins, polypeptides and capsomeres produced for use as vaccines or as diagnostic agents can be confirmed by reaction with antibodies or monoclonal antibodies that react or recognize conformational epitopes present on the intact version of virus and based on ability to elicit the production of neutralizing antiserum. Other suitable assays for determining whether neutralizing antibodies are produced are known in the art and contemplated herein. This characteristic of HPV capsid proteins or other viral capsid proteins are essential for use in HPV or other viral vaccines.

In certain embodiments, target HPV proteins and polypeptides are used to generate immunogenic compositions against HPV infection. In accordance with these embodiments, these immunogenic compositions can contain proteins and/or capsomeres produced using constructs described herein in sufficient quantities to produce enough capsomeres that induce formation of neutralizing antibodies when introduced to a subject in need thereof. Immunogenic or vaccine compositions contemplated herein can further contain a pharmaceutically acceptable carrier or another anti-viral agent or other known agent in the art to compliment the composition.

Embodiments herein can include polypeptides that elicit an immune response to an HPV antigen in a subject. An elicited immune response may be either prophylactic, preventing later infection by the specific viral type targeted, or may be therapeutic, reducing the severity of infection or disease. An immune response can include a humoral, e.g., antibody, response to a provided antigen and/or a cell mediated response to a provided antigen in a vaccine. Methods to measure an immune response are known to those skilled in the art. If one or both types of immune response are present, they can protect a subject from developing the condition. In accordance with certain embodiments, ability of a composition disclosed herein to protect from disease refers to the ability of a capsomere or chimeric protein generated herein to treat, ameliorate and/or prevent disease caused by a virus contemplated herein or cross reactive agent, for example, by eliciting an immune response in the subject. It is to be noted that a subject may be protected by a composition of the present invention even without the detection of a humoral or cell-mediated response to the composition. Protection can be measured by methods known to those skilled in the art.

In other embodiments, as more than one HPV type may be associated with HPV infections, the immunogenic compositions or vaccines may include stable HPV capsid proteins derived from more than one type of HPV. In accordance with these embodiments, since HPV 16 and 18 are associated with cervical carcinomas as well as cancers that affect male subjects, a vaccine against developing cervical neoplasia can include capsomeres generated from constructs disclosed herein from HPV 16, HPV 18, or both HPV 16 and 18. A variety of neoplasias are known to be associated with HPV infections. For example, HPVs 3a and 10 have been associated with flat warts. A number of HPV types have been reported to be associated with epidermodysplasia verruciformis (EV) including HPVs 3a, 5, 8, 9, 10, and 12. HPVs 1, 2, 4, and 7 have been reported to be associated with cutaneous warts and HPVs 6b, 11a, 13, and 16 are associated with lesions of the mucus membranes. Other forms of cancer can also occur in the anus as well as in in the mouth and/or throat of affected subjects. Vaccine formulations disclosed herein can include a mixture of capsid proteins or fragments derived from different HPV types depending upon the desired protection. These formulations can be used to reduce the risk of onset or the treat a subject having a condition attributed to one or more HPV type.

Yet another aspect includes a method to elicit an immune response to a protein or capsomere generated herein in a subject by administering to the subject a composition described in certain embodiments herein. Immunogenic compositions or vaccines can be administered in therapeutically effective amounts. That is, in amounts sufficient to produce a protective immunological response. In accordance with these embodiments dosages ranging from about 0.1 mg protein to about 20 mg protein, more generally about 0.001 mg to about 1 mg protein can be introduced to a subject in need thereof or to a subject in order to reduce the onset of a condition associated with infection (e.g. HPV infection). Single or multiple dosages can be administered as determined by a health professional.

In other embodiments, administration of capsomere-containing vaccines may be effected by any pharmaceutically acceptable means, e.g., parenterally, locally or systemically, including by way of example, oral drops or tablet, intranasal, intravenous, intramuscular, subcutaneous, inhalation, and topical administration. The manner of administration is affected by factors including the natural route of infection. The dosage administered will depend upon factors including the age, health, weight, kind of concurrent treatment, if any, and nature and type of the particular viral, e.g., human, papillomavirus. The vaccine or immunogenic composition may be employed in dosage form such as capsules, liquid solutions, suspensions, or elixirs, for oral administration, or sterile liquid formulations such as solutions or suspensions for parenteral or intranasal use.

Any pharmaceutical formulation known in the art for a vaccine is contemplated herein. It is contemplated that formulations can contain other agents of use in vaccination of a subject including, but not limited to other active or inactive ingredients or compositions known to one skilled in the art.

All contemplated vaccine compositions can be prepared by any method known to one skilled in the art. In certain embodiments, the virus compositions are lyophilized and are mixed with a pharmaceutically acceptable excipient (e.g. water, phosphate buffered saline (PBS), wetting agents etc.) In other embodiments, vaccine compositions can include stabilizers that are known to reduce degradation of the formulation and prolong shelf-life of the compositions.

In other embodiments, an adjuvant may be added to the composition to induce, increase, stimulate or strengthen a cellular or humoral immune response to administration of a vaccination described herein.

Any adjuvant known in the art that is compatible with compositions disclosed herein is contemplated. Adjuvants are typically substances that generally enhance the immune response of a patient to a specific antigen. Suitable antigens include, but are not limited to, other bacterial cell wall components, aluminum based salts, calcium based salts, silica, polynucleotides, toxins, such as cholera toxin, toxoids, such as cholera toxoid, serum proteins, other viral coat proteins, other bacterial-derived preparations, block copolymer adjuvants, and saponins and their derivatives.

Some embodiments herein concern amounts or doses or volume of administration of a vaccine or immunogenic composition contemplated herein and the amount or dose can depend on route of administration and other specifications such as the subject getting the vaccine (e.g. age, health condition, weight etc.)

Other embodiments concern kits of use with the methods (e.g. methods of generating constructs contemplated herein) and compositions described herein. Some embodiments concern kits having vaccine compositions of use to prevent or treat subjects having, exposed or suspected of being exposed to HPV. In certain embodiments, a kit may contain one or more than one formulation of HPV strain or type produced by methods disclosed herein (e.g. tagless methods). Kits can be portable, for example, able to be transported and used in remote areas such as military installations or remote villages. Other kits may be of use in a health facility to treat a subject having been exposed to or carrying HPV to induce their immune response.

Kits can also include a suitable container, for example, vials, tubes, mini- or microfuge tubes, test tube, flask, bottle, syringe or other container. Where an additional component or agent is provided, the kit can contain one or more additional containers into which this agent or component may be placed. Kits herein will also typically include a means for containing the agent, composition and any other reagent containers in close confinement for commercial sale. Such containers may include injection or blow-molded plastic containers into which the desired vials are retained. Optionally, one or more additional agents such as immunogenic agents or other anti-viral agents, anti-fungal or antibacterial agents may be needed for compositions described, for example, for compositions of use as a vaccine against one or more additional microorganisms.

In other embodiments, kits can include devices for administering one or more vaccination to a subject such as an intradermal, subcutaneous, intramuscular, inhaler or other device for administering a vaccine composition disclosed herein.

EXAMPLES

The following examples are included to demonstrate certain embodiments presented herein. It should be appreciated by those of skill in the art that the techniques disclosed in the examples that follow represent techniques discovered to function well in the practices disclosed herein. However, those of skill in the art should, in light of the present disclosure, appreciate that many changes can be made in the certain embodiments which are disclosed and still obtain a like or similar result without departing from the spirit and scope herein.

In certain exemplary methods below, the coding region for a truncated HPV L1 protein was amplified via PCR from an E. coli codon-optimized gene and cloned downstream of the pTac promoter to generate a tagless polypeptide when expressed in E. coli. Alternatively, the native HPV L1 gene could be used instead of the codon-optimized version. Also, the full length L1 coding region or other truncated gene versions could be used for the expression construct. In some exemplary methods, it may be possible to use endogenous restriction endonuclease sites, instead of PCR, to generate the L1 coding region. Suitable regulatory sequences for achieving cloning and expression, e.g., promoters, and selectable markers are well known in the art. The essential requirements for protein expression from a plasmid construct in bacteria are a promoter (e.g., pLac, pTac, or pT7), a selectable marker (e.g., kanamycin resistance) and an origin of replication. Thus, a modified construct contemplated herein can be composed of HPV DNA capable of encoding a polypeptide, an antibiotic resistance gene and additional filler sequences.

In these examples, E. coli HMS174 (DE3) cells (Novagen) were used for protein expression. In addition, E. coli BL21 (DE3) or BLR (DE3) cells (Novagen) have been used to express the HPV L1 constructs. Since the HPV-p3 plasmid utilizes a pTac promoter for expression, the DE3 lysogen (encoding T7 RNA polymerase) in the above listed E. coli cells is not necessary here. For example, E. coli HMS174 cells (Novagen) could be used as well as other known cells. Also, expression conditions (e.g. induction temperature, IPTG concentration or culture density) can be modified to improve L1 expression and subsequent yield.

HPV L1 Tagless Plasmid Construct.

FIG. 1 illustrates a map of an exemplary plasmid of certain embodiments disclosed herein. Fragments of the plasmid originated from other plasmids as noted. The HPV16 L1 coding region for a truncated HPV L1 protein was amplified via PCR from an E. coli codon-optimized gene with NdeI and XhoI restriction sites to facilitate cloning. Kan refers to the kanamycin resistance gene.

Figure 2:
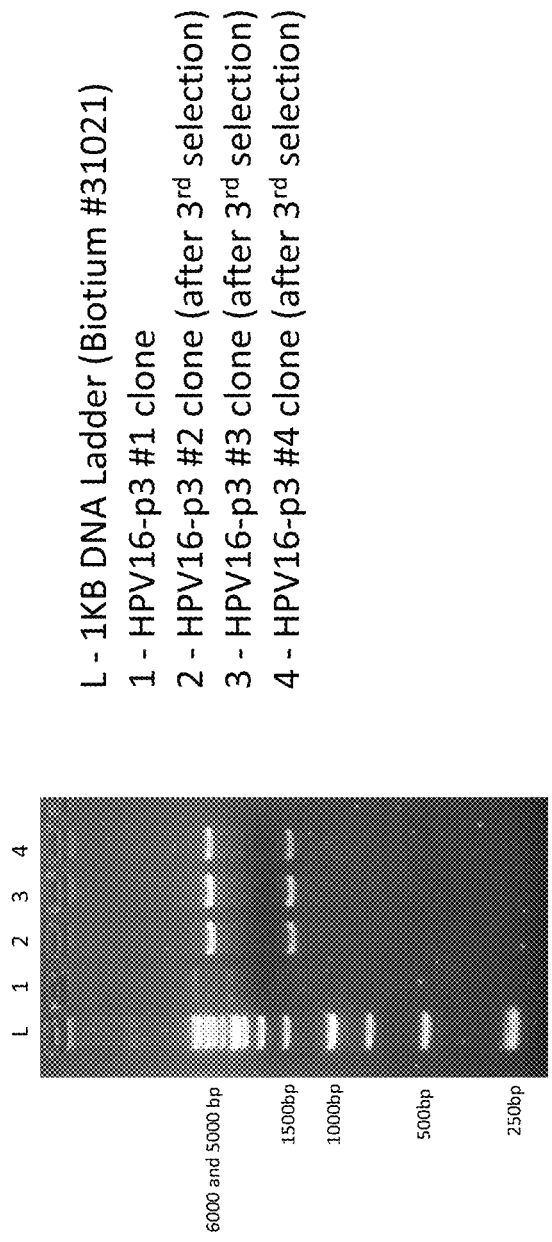
FIG. 2 represents an image of an agarose electrophoresis gel separation of plasmid constructs represented by FIG. 1.

FIG. 2 represents an agarose gel electrophoretic separation of DNA fragments. The plasmid encoding HPV-16 L1 was transformed into E. coli to generate a clonal population of E. coli. This was performed on three occasions (#2, #3, #4 clone). The resulting plasmid was extracted from E. coli and digested with XhoI and NdeI to release a~1500 bp insert. This analysis is to confirm the presence of the L1 coding sequence. This is a diagnostic analysis to confirm the identity of this expression plasmid.

Figure 3:
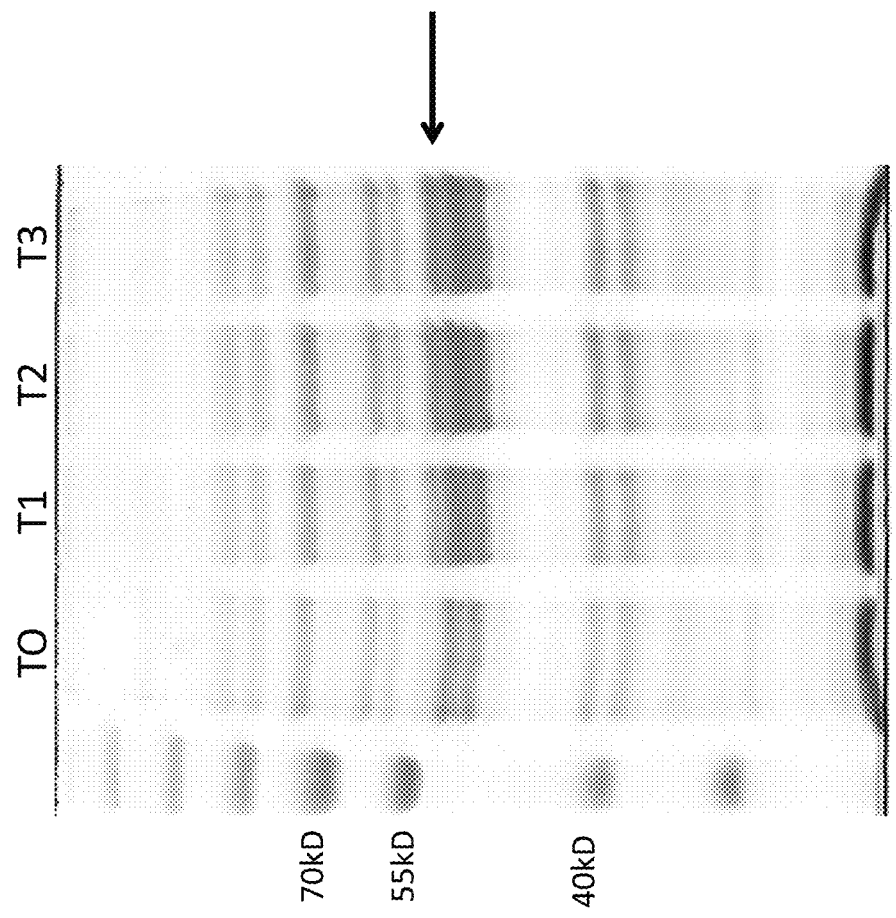
FIG. 3 represents an image of a representative SDS-PAGE demonstrating expression/induction of L1 protein in *E. coli*. Time of induction is indicated on the top panel (in hours). The position of L1 is indicated by the arrow.
Figure 6A:
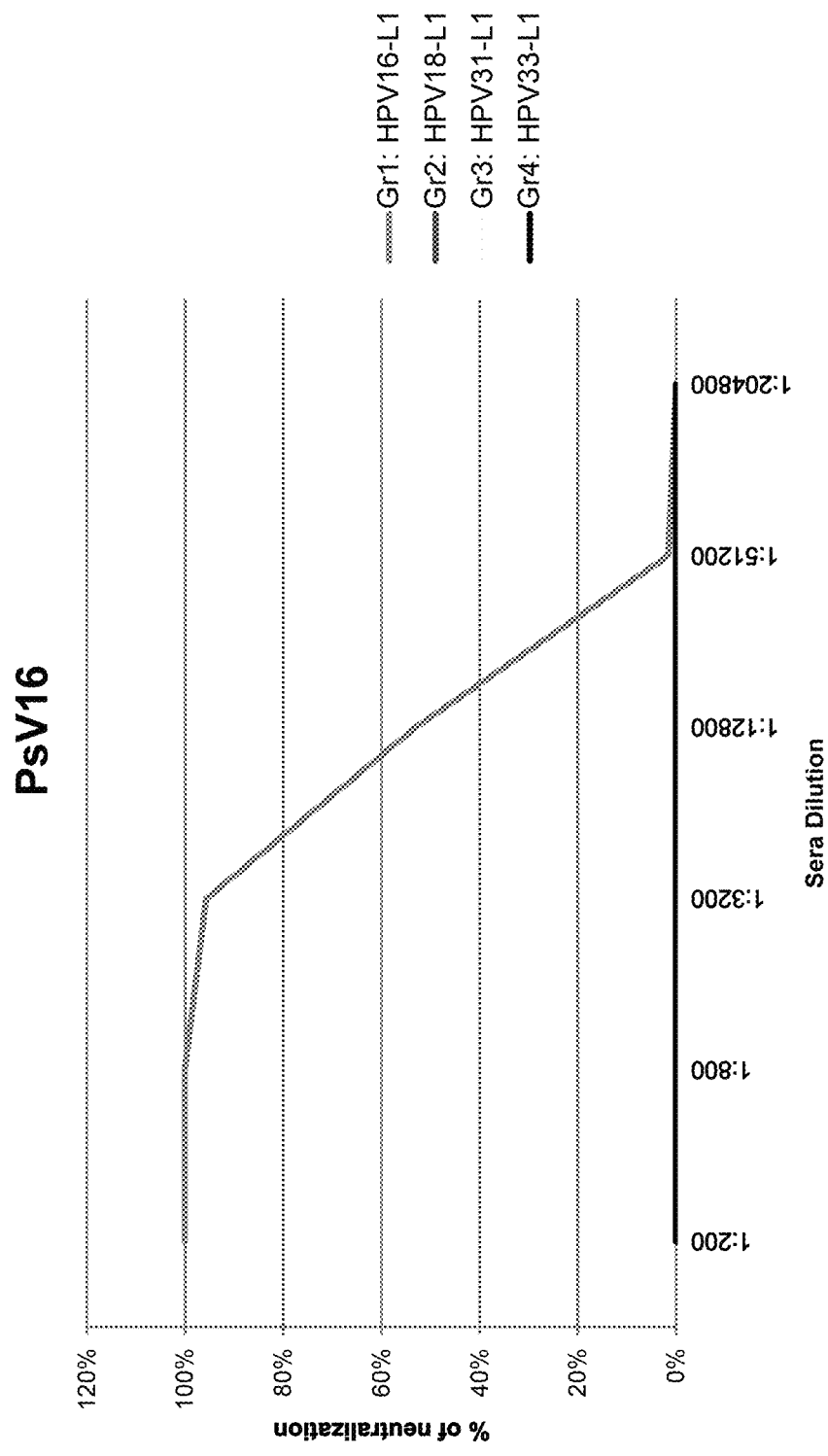
Figure 6B:
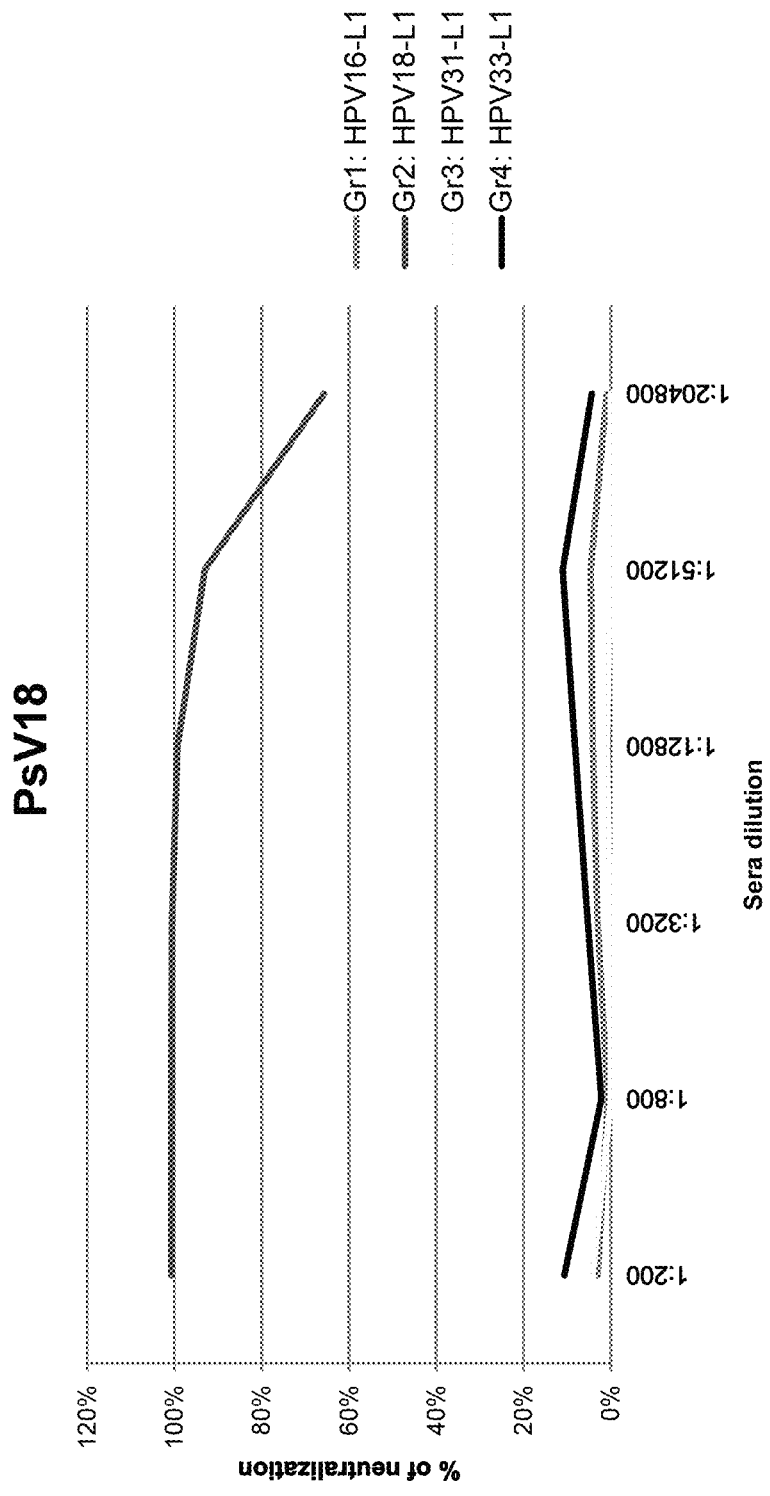
Figure 6D:
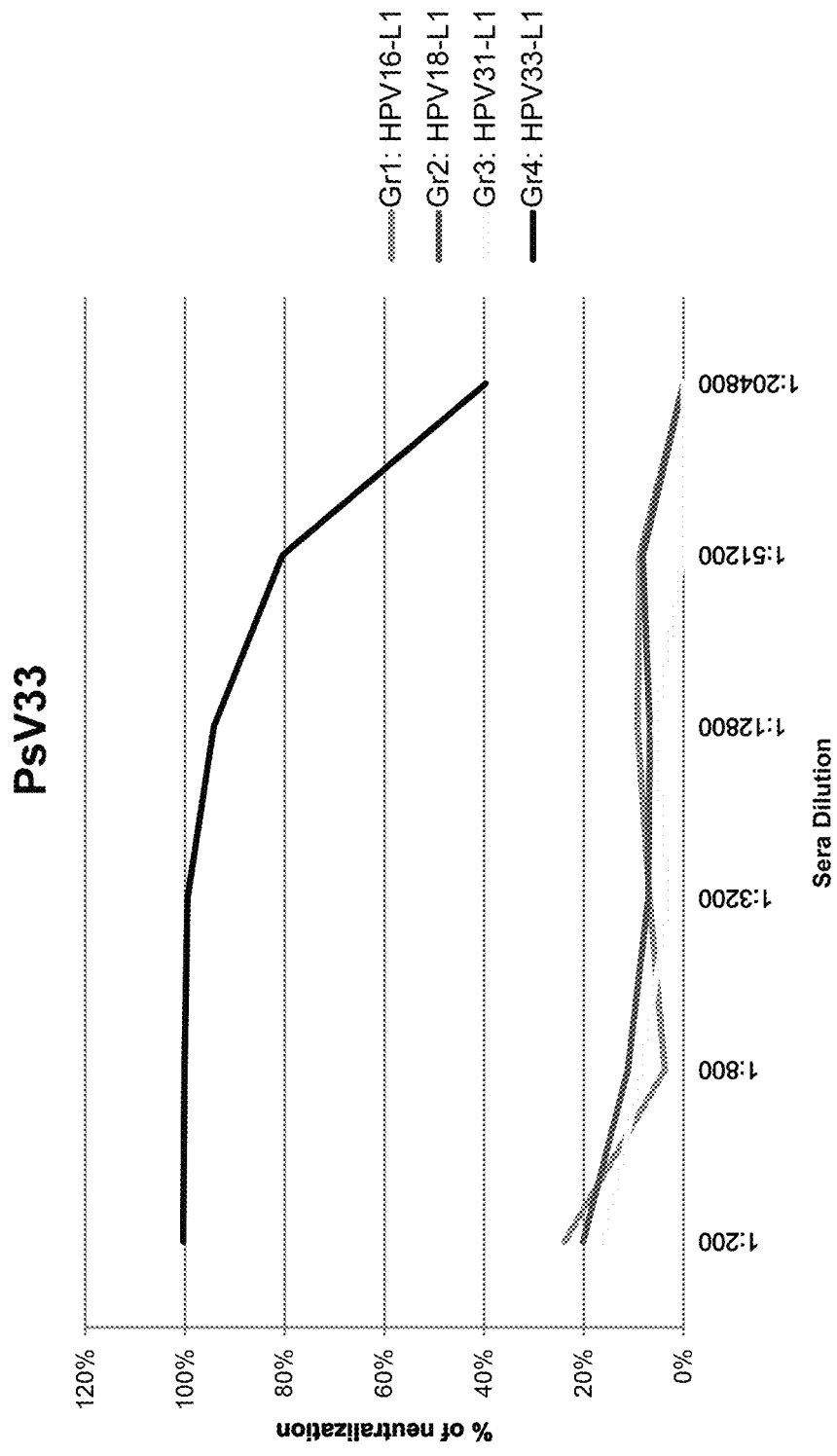

FIG. 3 represents an image of gel electrophoresis separation of proteins produced by tagless constructs generated by methods known in the art, prior to isolation of the target protein. The arrow indicates migration of the L1 protein band. E. coli were induced with addition of IPTG to express the L1 protein (indicated by the red arrow at approximately 52 kDa). Protein induction was carried out for three hours, and samples were taken at 1 hour, 2 hours and 3 hours (T1, T2, T3) and separated by SDS-PAGE, followed by staining with commassie blue.

FIG. 4 represents ELISA reactivity with V5 conformational Antibody. The V5 monoclonal Ab is known to react with epitopes on HPVL1 corresponding to the sites where neutralizing antibodies bind the HPV16-L1 pentamer. Purified L1 protein was serially diluted as noted. Absorbance increases with increasing V5 binding. Reactivity with the antibody confirms the pentameric structure of the HPV-L1 tagless protein. The V5 monoclonal Ab is known to react with epitopes on HPVL1 corresponding to the sites where neutralizing antibodies bind the HPV16-L1 pentamer FIG. 5 represents a quaternary structure of HPV16-L1: Electron micrograph confirming characteristic pentamer formation. Purified protein was applied to electron microscope grids and negatively stained with uranyl acetate.

FIGS. 6A-6D represent exemplary Pseudovirus neutralization assays. Sera from mice injected with purified L1 protein (Gr 1-4 as noted) were tested for the ability to neutralize Pseudovirus-mediated (PsV) reporter gene expression from 4 different PSV types as shown. Gr1, Gr2, Gr3 and Gr4 mice were injected with HPV16 (6A), HPV18 (6B), HPV31 (6C) and HPV33 (6D) L1 capsomeres, respectively. These results illustrate that L1 protein expressed and purified as described can induce specific neutralizing antibodies in mice.

FIGS. 7A-7C-FIG. 11: WCL=whole cell lysate, S1=soluble fraction, P1=insoluble pellet. The arrow indicates migration of the L1 protein band.

FIGS. 7A-7C represent images of representative SDS-PAGE gels demonstrating expression of HPV16L1 with N-terminal deletions of 3 (7A), 5 (7B) or 9 (7C) amino acids.

FIG. 8 represents an image of a representative SDS-PAGE demonstrating expression of HPV16L1 with N-terminal deletions of 13 or 15 amino acids.

Figure 9:
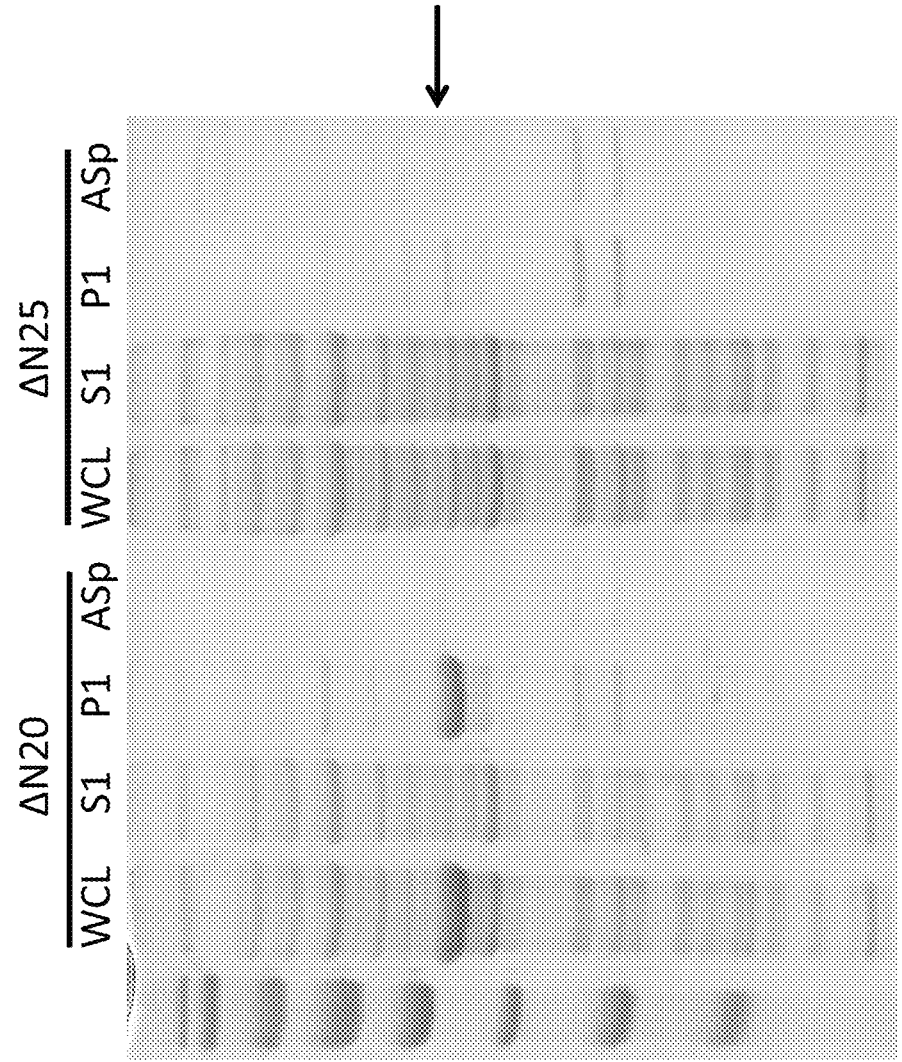
FIG. 9 represents an image of a representative SDS-PAGE demonstrating expression of HPV16L1 with N-terminal deletions of 20 or 25 amino acids.

FIG. 9 represents an image of a representative SDS-PAGE demonstrating expression of HPV16L1 with N-terminal deletions of 20 or 25 amino acids.

Figures 10A, 10B:
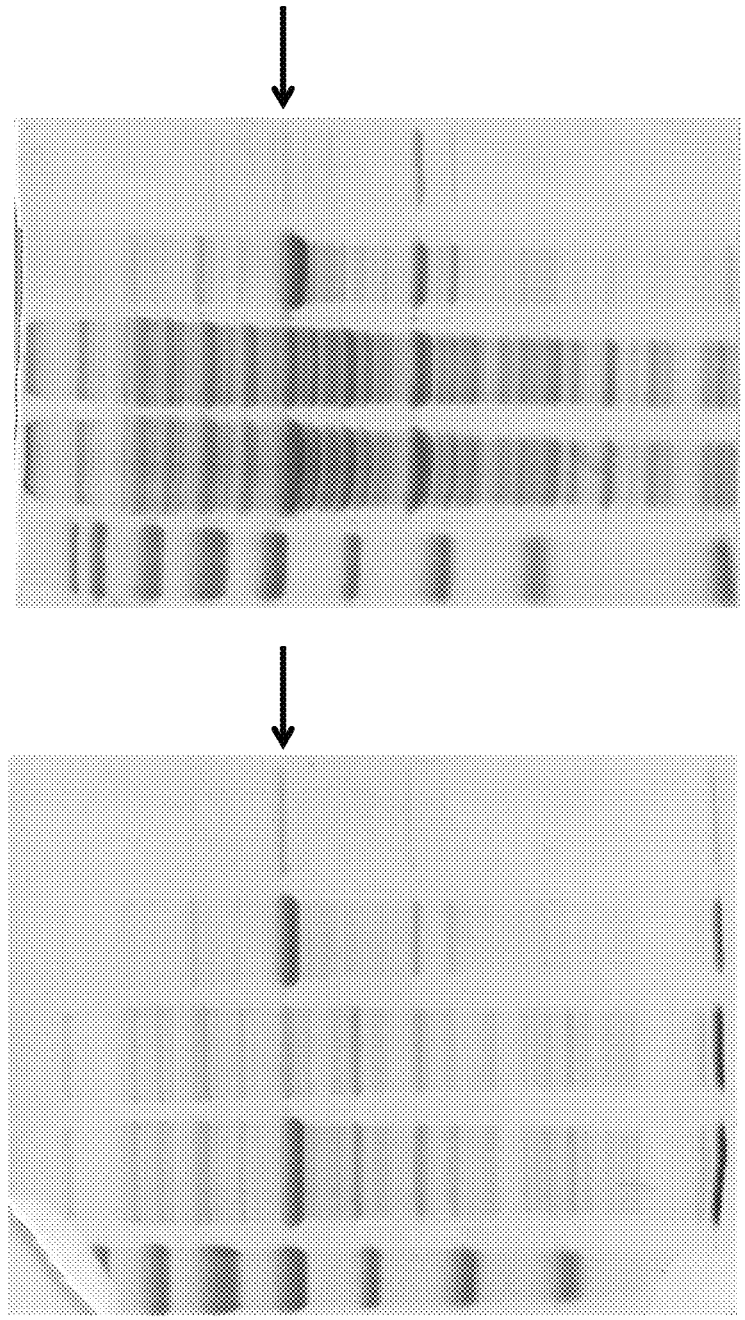
FIGS. 10A-10B represents an image of a representative SDS-PAGE demonstrating expression of HPV18L1 with N-terminal deletions of 5 (10A) or 9 (10B) amino acids.

FIGS. 10A-10B represent images of representative SDS-PAGE gels demonstrating expression of HPV18L1 with N-terminal deletions of 5 (10A) or 9 (10B) amino acids.

FIG. 11 represents an image of a representative SDS-PAGE demonstrating expression of HPV18L1 with N-terminal deletions of 15 or 16 amino acids.

Materials and Methods

Plasmid Construction

Methods known in the art were used to produce a construct illustrated in FIG. 1. Individual DNA sequences encoding the L1 proteins of HPV types 16, 18, 31, 33, 35, 45, 52 and 58 were codon optimized for *E. coli* and chemically synthesized (GenScript). Truncated sequences of these L1 genes, flanked by NdeI and XhoI restriction sites, were generated by PCR, digested with NdeI and XhoI, and ligated to the pET-TAC plasmid backbone (see FIG. 1). A plasmid (pET-TAC E7L1, Biosidus) encoding a GST-hexahistidine-HPV16 L1/E7 fusion protein under the control of a pTac promoter was restriction digested with NdeI and XhoI to separate the plasmid backbone from the L1/E7 fusion protein cassette. The plasmid backbone contains the pTac promoter, a Kanamycin resistance gene and an *E. coli* origin of replication (see FIG. 1). The L1/E7 fragment was discarded. The NdeI site encodes an "ATG" that is used as the initiation site for translation. Alternatively an NcoI site can also be used. For PCR, the 5' oligonucleotide "AGTAGTCATATGACCGTGTATCTGCCGCC" (SEQ ID NO:9) was used in each reaction. To generate the truncated coding region for HPV16, HPV33 or HPV35 L1, the oligonucleotide "ATCTCGAGTTATTACGCTTTCAGGCCCGCC" (SEQ ID NO: 10) was also used in PCR. The second oligonucleotide used for PCR to generate the truncated L1 coding region for the other serotypes were

```
                                       (SEQ ID NO: 11)
"ATCTCGAGTTATTAACGACGCAGGCCCGCC" for HPV18, (SEQ ID NO: 12)
"ATCTCGAGTTATTACGCACGATAGCCCGCC" for HPV31, (SEQ ID NO: 13)
"ATCTCGAGTTATTATCGACGCAGACCTGCC" for HPV45, (SEQ ID NO: 14)
"ATCTCGAGTTATTATGCCTGCAGACCTGCC" for HPV52,
and (SEQ ID NO:15)
"ATCTCGAGTTATTACGCTTTCAGGCCGCTC" for HPV58.
```

An aliquot from each ligation reaction was used to transform *E. coli* HMS174 (DE3) cells (Novagen). The truncated DNA sequences encode L1 protein with deletions of the coding region for the N-terminal 9 amino acids and the C-terminal 29 amino acids (based on the HPV 16 L1 sequence). All plasmid constructs (termed "HPV16-p3", "HPV18-p3", "HPV31-p3", etc.) were verified by DNA sequence analysis. The DNA sequences encoding the truncated L1 proteins (not including the ATG) are:

HPV16-p3

(SEQ ID NO: 1)
"ACCGTGTATCTGCCGCCGGTGCCTGTGAGCAAAGTTGTGAGCACCGATGA

ATATGTGGCGCGTACCAACATTTATTATCATGCGGGCACCAGCCGTCTGCT

GGCGGTGGGCCATCCGTATTTTCCGATCAAGAAACCGAACAACAACAAAT

TCTGGTGCCGAAAGTGAGCGGCCTGCAGTATCGTGTGTTTCGTATTCATCT

GCCTGATCCAAACAAATTTGGCTTTCCGGATACCAGCTTTTATAACCCGGA

TACCCAGCGTCTGGTGTGGGCATGCGTGGGTGTGGAAGTGGGTCGTGGTCA

GCCGCTGGGTGTGGGCATTAGCGGCCATCCGCTGCTGAACAAACTGGATGA

TACCGAAAACGCGAGCGCGTATGCGGCGAACGCGGGCGTGGATAACCGTGA

ATGCATTAGCATGGATTATAAACAGACCCAGCTGTGCCTGATTGGCTGCAA

ACCGCCGATTGGCGAACATTGGGGTAAAGGCAGCCCGTGCACCAACGTGGC

AGTGAACCCGGGTGATTGCCCGCCGCTGGAACTGATTAACACCGTGATTCA

GGATGGCGATATGGTGGATACCGGCTTTGGCGCGATGGATTTTACCACCCT

GCAGGCGAACAAAAGCGAAGTGCCGCTGGATATTTGCACCAGCATTTGCAA

ATATCCGGATTATATTAAAATGGTTAGCGAACCGTATGGCGATAGCCTGTT

TTTCTACCTGCGTCGTGAACAGATGTTTGTGCGTCATCTGTTTAACCGTGC

GGGCGCGGTGGGCGAAAACGTGCCGGATGATCTGTATATTAAAGGCAGCGG

CAGCACCGCGAACCTGGCGAGCAGCAACTATTTTCCGACCCCGAGCGGCAG

CATGGTGACCAGCGATGCGCAGATTTTTAACAAACCGTATTGGCTGCAGCG

TGCGCAGGGCCATAACAACGGCATTTGCTGGGGCAACCAGCTGTTTGTGAC

CGTGGTGGATACCACCCGTAGCACCAACATGAGCCTGTGCGCGGCGATTAG

CACCAGCGAAACCACCTATAAAAACACCAACTTTAAAGAATATCTGCGTCA

TGGCGAAGAATATGATCTGCAGTTTATTTTTCAGCTGTGCAAAATTACCCT

GACCGCGGATGTGATGACCTATATTCATAGCATGAACAGCACCATTCTGGA

AGATTGGAACTTTGGCCTGCAGCCGCCGCCGGGCGGCACCCTGGAAGATAC

CTATCGTTTTGTGACCAGCCAGGCGATTGCGTGCCAGAAACATACCCCGCC

GGCGCCGAAAGAAGATCCGCTGAAAAAATATACCTTTTGGGAAGTGAACCT

GAAAGAAAAATTTAGCGCGGATCTGGATCAGTTTCCGCTGGGCCGTAAATT

TCTGCTGCAGGCGGGCCTGAAAGCG"

HPV18-p3

(SEQ ID NO: 2)
"ACCGTGTATCTGCCGCCGCCGAGCGTGGCGCGTGTGGTGAACACCGATGA

TTATGTGACCCGCACCAGCATCTTCTACCATGCGGGCAGCAGCCGTCTGCT

GACCGTGGGCAACCCGTATTTTCGTGTGCCGGCAGGTGGAGGCAACAAACA

GGATATTCCGAAAGTGAGCGCGTATCAGTATCGTGTGTTTCGTGTGCAGCT

GCCTGATCCAAACAAATTTGGCCTGCCGGATACCAGCATTTATAACCCGGA

AACCCAGCGTCTGGTGTGGGCATGCGCCGGTGTGGAAATTGGTCGTGGTCA

GCCGCTGGGTGTGGGTCTGAGCGGTCATCCGTTTTATAACAAACTGGATGA

TACCGAAAGCAGCCATGCGGCGACCAGCAACGTGAGCGAAGATGTGCGTGA

TAACGTGAGCGTGGATTATAAACAGACCCAGCTGTGCATTCTGGGCTGCGC

GCCGGCGATTGGCGAACATTGGGCAAAAGGTACCGCATGCAAAAGCCGTCC

GCTGAGCCAGGGCGATTGCCCGCCGCTGGAACTGAAAAACACCGTGCTGGA

AGATGGCGATATGGTGGATACCGGCTATGGCGCGATGGATTTTAGCACCCT

GCAGGATACCAAATGCGAAGTGCCGCTGGATATTTGCCAGAGCATTTGCAA

ATATCCGGATTATCTGCAGATGAGCGCAGATCCATATGGCGATAGCATGTT

TTTCTGCCTGCGTCGTGAACAGCTGTTTGCGCGTCATTTTTGGAACCGTGC

GGGCACCATGGGCGATACCGTGCCGCAGAGCCTGTATATTAAAGGTACCGG

TATGCGCGCAAGCCCGGGCAGCTGCGTGTATAGCCCGAGCCCGAGCGGCAG

CATTGTGACCAGCGATAGCCAGCTGTTTAACAAACCGTATTGGCTGCATAA

AGCGCAGGGCCATAACAACGGCGTGTGCTGGCATAACCAGCTGTTTGTGAC

CGTGGTGGATACCACCCGCAGCACCAACCTGACCATTTGCGCGAGCACCCA

GAGCCCGGTGCCGGGCCAGTATGATGCGACCAAATTTAAACAGTATAGCCG

-continued

TCATGTGGAAGAATATGATCTGCAGTTTATTTTTCAGCTGTGCACCATTAC

CCTGACCGCGGATGTGATGAGCTATATTCATAGCATGAACAGCAGCATTCT

GGAAGATTGGAACTTTGGCGTGCCGCCGCCGCCGACCACCAGCCTGGTGGA

TACCTATCGTTTTGTGCAGAGCGTGGCGATTACCTGCCAGAAAGATGCGGC

GCCGGCGGAAAACAAAGATCCGTACGATAAACTGAAATTCTGGAACGTGGA

TCTGAAAGAAAAATTCAGCCTGGATCTGGATCAGTATCCGCTGGGCCGTAA

ATTTCTGGTGCAGGCGGGCCTGCGTCGT"

HPV31-p3
(SEQ ID NO: 3)
"ACCGTGTATCTGCCGCCGGTGCCTGTGAGCAAAGTTGTGAGCACCGATGA

ATATGTGACCCGTACCAACATTTATTATCATGCGGGCAGCGCGCGTCTGCT

GACCGTGGGCCATCCGTATTATAGCATTCCGAAAAGCGATAACCCAAAGAA

AATCGTGGTGCCGAAAGTGAGCGGCCTGCAGTATCGTGTGTTTCGTGTGCG

TCTGCCTGATCCAAACAAATTTGGCTTTCCGGATACCAGCTTTTATAACCC

GGAAACCCAGCGTCTGGTGTGGGCATGCGTGGGTCTGGAAGTGGGTCGTGG

TCAGCCGCTGGGTGTGGGCATTAGCGGCCATCCGCTGCTGAACAAATTTGA

TGATACCGAAAACAGCAACCGTTATGCAGGTGGACCGGGCACCGATAACCG

TGAATGCATTAGCATGGATTATAAACAGACCCAGCTGTGCCTGCTGGGCTG

CAAACCGCCGATTGCCGAACATTGGGGCAAAGGCAGCCCGTGCAGCAACAA

CGCGATTACCCCGGGCGATTGCCCGCCGCTGGAACTGAAAAACAGCGTGAT

TCAGGATGGCGATATGGTGGATACCGGCTTTGGCGCGATGGATTTTACCGC

GCTGCAGGATACCAAAAGCAACGTGCCGCTGGATATTTGCAACAGCATTTG

CAAATATCCGGATTATCTGAAAATGGTGGCGGAACCGTATGGCGATACCCT

GTTTTTCTACCTGCGTCGTGAACAGATGTTTGTGCGTCATTTCTTTAACCG

TAGCGGCACCGTGGGCGAAAGCGTGCCGACCGATCTGTATATTAAAGGCAG

CGGCAGCACCGCGACCCTGGCGAACAGCACCTATTTTCCGACCCCGAGCGG

CAGCATGGTGACCAGCGATGCGCAGATTTTTAACAAACCGTATTGGATGCA

GCGTGCGCAGGGCCATAACAACGGCATTTGCTGGGGCAACCAGCTGTTTGT

GACCGTGGTGGATACCACCCGTAGCACCAACATGAGCGTGTGCGCGGCGAT

TGCGAACAGCGATACCACCTTTAAAAGCAGCAACTTTAAAGAATATCTGCG

TCATGGCGAAGAATTTGATCTGCAGTTTATTTTTCAGCTGTGCAAAATTAC

CCTGAGCGCGGATATTATGACCTATATTCATAGCATGAACCCGGCGATTCT

GGAAGATTGGAACTTTGGCCTGACCACCCCGCCGAGCGGCAGCCTGGAAGA

TACCTATCGTTTTGTGACCAGCCAGGCGATTACCTGCCAGAAAACCGCGCC

GCAGAAACCGAAAGAAGATCCGTTTAAAGATTATGTGTTTGGGAAGTGAA

CCTGAAAGAAAAATTTAGCGCGGATCTGGATCAGTTTCCGCTGGGCCGTAA

ATTTCTGCTGCAGGCGGGCTATCGTGCG"

HPV33-p3
(SEQ ID NO: 4)
"ACCGTGTATCTGCCGCCGGTGCCTGTGAGCAAAGTTGTGAGCACCGATGA

ATATGTGAGCCGTACCAGCATTTATTATTATGCGGGCAGCAGCCGTCTGCT

GGCGGTGGGCCATCCGTATTTTAGCATTAAAAAACCCGACCAACGCGAAAA

ACTGCTGGTGCCGAAAGTGAGCGGCCTGCAGTATCGTGTGTTTCGTGTGCG

TCTGCCTGATCCAAACAAATTTGGCTTTCCGGATACCAGCTTTTATAACCC

GGATACCCAGCGTCTGGTGTGGGCATGCGTGGGTCTGGAAATTGGTCGTGG

TCAGCCGCTGGGTGTGGGTATTAGCGGTCATCCGCTGCTGAACAAATTTGA

TGATACCGAAACCGGCAACAAATATCCGGGCCAGCCGGGCGCGGATAACCG

TGAATGCCTGAGCATGGATTATAAACAGACCCAGCTGTGCCTGCTGGGCTG

CAAACCGCCGACCGGTGAACATTGGGGTAAAGGCGTGGCATGCACCAACGC

AGCACCGGCAAACGATTGCCCGCCGCTGGAACTGATTAACACCATTATTGA

AGATGGCGATATGGTGGATACCGGCTTTGGCTGCATGGATTTTAAAACCCT

GCAGGCGAACAAAAGCGATGTGCCGATTGATATTTGCGGCAGCACCTGCAA

ATATCCGGATTATCTGAAAATGACCAGCGAACCGTATGGCGATAGCTTGTT

CTTTTTCCTGCGTCGAGAACAGATGTTTGTGCGTCATTTCTTTAACCGTGC

GGGCACCCTGGGCGAAGCGGTGCCGGATGATCTGTATATTAAAGGCAGCGG

CACCACCGCGAGCATTCAGAGCAGCGCATTTTTCCCGACCCCGAGCGGCAG

CATGGTGACCAGCGAAAGCCAGCTGTTTAACAAACCGTATTGGCTGCAGCG

TGCGCAGGGCCATAACAACGGCATTTGCTGGGGCAACCAGGTGTTTGTGAC

CGTGGTGGATACCACCCGTAGCACCAACATGACCCTGTGCACCCAGGTGAC

CAGCGATAGCACCTACAAAAACGAAAACTTCAAAGAATACATCCGTCATGT

GGAAGAATACGATCTGCAGTTCGTGTTTCAGCTGTGCAAAGTGACCCTGAC

CGCGGAAGTGATGACCTATATTCATGCGATGAACCCGGATATTCTGGAAGA

TTGGCAGTTTGGCCTGACCCCGCCGCCGAGCGCGAGCCTGCAGGATACCTA

TCGTTTTGTGACCAGCCAGGCGATTACCTGCCAGAAAACCGTGCCGCCGAA

AGAAAAAGAAGATCCGCTGGGCAAATATACCTTTTGGGAAGTGGATCTGAA

AGAAAAATTTAGCGCGGATCTGGATCAGTTTCCGCTGGGCCGTAAATTTCT

GCTGCAGGCGGGCCTGAAAGCG"

HPV35-p3
(SEQ ID NO: 5)
"ACCGTGTATCTGCCGCCTGTGAGCGTGAGCAAAGTTGTGAGCACCGATGA

ATATGTGACCCGTACCAACATTTATTATCATGCGGGCAGCAGCCGTCTGCT

GGCGGTGGGCCATCCGTATTATGCGATCAAGAAACAGGATAGCAACAAAAT

TGCGGTGCCGAAAGTGAGCGGCCTGCAGTATCGTGTGTTTCGTGTGAAACT

GCCTGATCCAAACAAATTTGGCTTTCCGGATACCAGCTTTTATGATCCGGC

AAGCCAGCGTCTGGTGTGGGCATGCACCGGTGTGGAAGTGGGTCGTGGTCA

GCCGCTGGGCGTGGGCATTAGCGGCCATCCGCTGCTGAACAAACTGGATGA

TACCGAAAACAGCAACAAATATGTGGGCAACAGCGGCACCGATAACCGTGA

ATGCATTAGCATGGATTATAAACAGACCCAGCTGTGCCTGATTGGCTGCCG

TCCGCCGATTGGCGAACATTGGGGCAAAGGCACCCCGTGCAACGCGAACCA

GGTGAAAGCGGGCGAATGCCCGCCGCTGGAACTGCTGAACACCGTGCTGCA

GGATGGCGATATGGTGGATACCGGCTTTGGCGCGATGGATTTTACCACCCT

GCAGGCGAACAAAAGCGATGTGCCGCTGGATATTTGCAGCAGCATTTGCAA

ATATCCGGATTATCTGAAAATGGTTAGCGAACCGTATGGCGATATGCTGTT

TTTCTACCTGCGTCGTGAACAGATGTTTGTGCGTCATCTGTTTAACCGTGC

-continued

GGGCACCGTGGGCGAAACCGTGCCGGCGGATCTGTATATTAAAGGCACCAC

CGGCACCCTGCCGAGCACCAGCTATTTTCCGACCCCGAGCGGCAGCATGGT

GACCAGCGATGCGCAGATTTTTAACAAACCGTATTGGCTGCAGCGTGCGCA

GGGCCATAACAACGGCATTTGCTGGAGCAACCAGCTGTTTGTGACCGTGGT

GGATACCACCCGTAGCACCAACATGAGCGTGTGCAGCGCGGTGTCTAGTAG

CGATAGCACCTATAAAAACGATAACTTTAAAGAATATCTGCGTCATGGCGA

AGAATATGATCTGCAGTTTATTTTTCAGCTGTGCAAAATTACCCTGACCGC

GGATGTGATGACCTATATTCATAGCATGAACCCGAGCATTCTGGAAGATTG

GAACTTTGGCCTGACCCCGCCGCCGAGCGGCACCCTGGAAGATACCTATCG

TTATGTGACCAGCCAGGCGGTGACCTGCCAGAAACCGAGCGCGCCGAAACC

GAAAGATGATCCGCTGAAAAACTATACCTTTTGGGAAGTGGATCTGAAAGA

AAAATTTAGCGCGGATCTGGATCAGTTTCCGCTGGGCCGTAAATTTCTGCT

GCAGGCGGGCCTGAAAGCG"

HPV45-p3

(SEQ ID NO: 6)

"ACCGTGTATCTGCCGCCGCCGAGCGTGGCGCGTGTGGTTAGCACCGATGA

TTATGTGAGCCGTACCAGCATCTTCTACCATGCGGGCAGCAGCCGTCTGCT

GACCGTGGGCAACCCGTATTTTCGTGTGGTGCCGAACGGCGCGGGCAACAA

ACAGGCGGTGCCGAAAGTGAGCGCGTATCAGTATCGTGTGTTTCGTGTGGC

GCTGCCTGATCCAAACAAATTTGGCCTGCCGGATAGCACCATTTATAACCC

GGAAACCCAGCGTCTGGTGTGGGCATGCGTGGGTATGGAAATTGGTCGTGG

TCAGCCGCTGGGTATTGGTCTGAGCGGTCATCCGTTTTATAACAAACTGGA

TGATACCGAAAGCGCGCATGCGGCGACCGCGGTGATTACCCAGGATGTGCG

TGATAACGTGAGCGTGGATTATAAACAGACCCAGCTGTGCATTCTGGGCTG

CGTGCCGGCGATTGGCGAACATTGGGCAAAAGGTACCCTGTGCAAACCGGC

ACAGCTGCAGCCGGGTGATTGCCCGCCGCTGGAACTGAAAAACACCATTAT

TGAAGATGGCGATATGGTGGATACCGGCTATGGCGCGATGGATTTTAGCAC

CCTGCAGGATACCAAATGCGAAGTGCCGCTGGATATTGCCAGAGCATTTG

CAAATATCCGGATTATCTGCAGATGAGCGCAGATCCATATGGCGATAGCAT

GTTTTTTCTGCTGCGTCGTGAACAGCTGTTTGCGCGTCATTTTTGGAACCG

TGCGGGCGTGATGGGCGATACCGTGCCGACCGATCTGTATATTAAAGGCAC

CAGCGCGAACATGCGTGAAACCCCGGGCAGCTGCGTGTATAGCCCGAGCCC

GAGCGGCAGCATTATTACCAGCGATAGCCAGCTGTTTAACAAACCGTATTG

GCTGCATAAAGCGCAGGGCCATAACAACGGCATTTGCTGGCATAACCAGCT

GTTTGTGACCGTGGTGGATACCACCCGTAGCACCAACCTGACCCTGTGCGC

GAGCACCCAGAACCCGGTGCCGAGCACCTATGATCCGACCAAATTTAAACA

GTATAGCCGTCATGTGGAAGAATATGATCTGCAGTTTATTTTTCAGCTGTG

CACCATTACCCTGACCGCGGAAGTGATGAGCTATATTCATAGCATGAACAG

CAGCATTCTGGAAAACTGGAACTTTGGCGTGCCGCCGCCGCCGACCACCAG

CCTGGTGGATACCTATCGTTTTGTGCAGAGCGTGGCGGTGACCTGCCAGAA

AGATACCACCCCGCCGGAAAAACAGGACCCATATGATAAACTGAAATTTTG

GACCGTGGATCTGAAAGAAAAATTTAGCAGCGATCTGGATCAGTATCCGCT

GGGCCGTAAATTTCTGGTGCAGGCAGGTCTGCGTCGA"

HPV52-p3

(SEQ ID NO: 7)

"ACCGTGTATCTGCCGCCGGTGCCTGTGAGCAAAGTTGTGAGCACCGATGA

ATATGTGAGCCGTACCAGCATTTATTATTATGCGGGCAGCAGCCGTCTGCT

GACCGTGGGCCATCCGTATTTTAGCATTAAAAACACCAGCAGCGGCAACGG

CAAAAAGTGCTGGTGCCGAAAGTGAGCGGCCTGCAGTATCGTGTGTTTCG

TATTAAACTGCCTGATCCAAACAAATTTGGCTTTCCGGATACCAGCTTTTA

TAACCCGGAAACCCAGCGTCTGGTGTGGGCATGCACCGGTCTGGAAATTGG

TCGTGGTCAGCCGCTGGGTGTGGGTATTAGCGGTCATCCGCTGCTGAACAA

ATTTGATGATACCGAAACCAGCAACAATATGCGGGCAAACCGGGCATTGA

TAACCGTGAATGCCTGAGCATGGATTATAAACAGACCCAGCTGTGCATTCT

GGGCTGCAAACCGCCGATTGGCGAACATTGGGGCAAAGGCACCCCGTGCAA

CAACAACAGCGGCAACCCGGGCGATTGCCCGCCGCTGCAGCTGATTAACAG

CGTGATTCAGGATGGCGATATGGTGGATACCGGCTTTGGCTGCATGGATTT

TAACACCCTGCAGGCGAGCAAAAGCGATGTGCCGATTGATATTTGCAGCAG

CGTGTGCAAATATCCGGATTATCTGCAGATGGCGAGCGAACCGTATGGCGA

TAGCTTGTTCTTTTTCCTGCGTCGAGAACAGATGTTTGTGCGTCATTTCTT

TAACCGTGCGGGCACCCTGGGCGATCCGGTGCCGGGCGATCTGTATATTCA

GGGCAGCAACAGCGGCAACACCGCGACCGTGCAGAGCAGCGCATTTTTCCC

GACCCCGAGCGGCAGCATGGTGACCAGCGAAAGCCAGCTGTTTAACAAACC

GTATTGGCTGCAGCGTGCGCAGGGCCATAACAACGGCATTTGCTGGGGCAA

CCAGCTGTTTGTGACCGTGGTGGATACCACCCGTAGCACCAACATGACCCT

GTGCGCGGAAGTGAAAAAGAAAGCACCTATAAAAACGAAAACTTTAAAGA

ATATCTGCGTCATGGCGAAGAATTTGATCTGCAGTTTATTTTTCAGCTGTG

CAAAATTACCCTGACCGCGGATGTGATGACCTATATTCATAAAATGGATGC

GACCATTCTGGAAGATTGGCAGTTTGGCCTGACCCCGCCGCCGAGCGCGAG

CCTGGAAGATACCTATCGTTTTGTGACCAGCACCGCGATTACCTGCCAGAA

AAACACCCCGCCGAAAGGCAAAGAAGATCCGCTGAAAGATTATATGTTTTG

GGAAGTGGATCTGAAAGAAAAATTTAGCGCGGATCTGGATCAGTTTCCGCT

GGGCCGTAAATTTCTGCTGCAGGCAGGTCTGCAGGCA"

HPV58-p3

(SEQ ID NO: 8)

"ACCGTGTATCTGCCGCCGGTGCCTGTGAGCAAAGTTGTGAGCACCGATGA

ATATGTGAGCCGTACCAGCATTTATTATTATGCGGGCAGCAGCCGTCTGCT

GGCGGTGGGCAACCCGTATTTTAGCATTAAAAGCCCGAACAACAACAAAAA

AGTGCTGGTGCCGAAAGTGAGCGGCCTGCAGTATCGTGTGTTTCGTGTGCG

TCTGCCTGATCCAAACAAATTTGGCTTTCCGGATACCAGCTTTTATAACCC

GGATACCCAGCGTCTGGTGTGGGCATGCGTGGGTCTGGAAATTGGTCGTGG

TCAGCCGCTGGGTGTGGGTGTGAGCGGTCATCCGTATCTGAACAAATTTGA

TGATACCGAAACCAGCAACCGTTATCCGGCGCAGCCGGGCAGCGATAACCG

TGAATGCCTGAGCATGGATTATAAACAGACCCAGCTGTGCCTGATTGGCTG

-continued

```
CAAACCGCCGACCGGCGAACATTGGGGCAAAGGCGTGGCGTGCAACAACAA

CGCGGCGGCGACCGATTGCCCGCCGCTGGAACTGTTTAACAGCATTATTGA

AGATGGCGATATGGTGGATACCGGCTTTGGCTGCATGGATTTTGGCACCCT

GCAGGCGAACAAAAGCGATGTGCCGATTGATATTTGCAACAGCACCTGCAA

ATATCCGGATTATCTGAAAATGGCGAGCGAACCGTATGGCGATAGCTTGTT

CTTTTTCCTGCGTCGAGAACAGATGTTTGTGCGTCATTTCTTTAACCGTGC

GGGCAAACTGGGCGAAGCGGTGCCGGATGATCTGTATATTAAAGGCAGCGG

CAACACCGCGGTGATTCAGAGCAGCGCATTTTTCCCGACCCCGAGCGGCAG

CATTGTGACCAGCGAAAGCCAGCTGTTTAACAAACCGTATTGGCTGCAGCG

TGCGCAGGGCCATAACAACGGCATTTGCTGGGGCAACCAGCTGTTTGTGAC

CGTGGTGGATACCACCCGTAGCACCAACATGACCCTGTGCACCGAAGTGAC

CAAAGAAGGCACCTATAAAAACGATAACTTTAAAGAATATGTGCGTCATGT

GGAAGAATATGATCTGCAGTTTGTGTTTCAGCTGTGCAAAATTACCCTGAC

CGCGGAAATTATGACCTATATTCATACCATGGATAGCAACATTCTGGAAGA

TTGGCAGTTTGGCCTGACCCCGCCGCCGAGCGCGAGCCTGCAGGATACCTA

TCGTTTTGTGACCAGCCAGGCGATTACCTGCCAGAAAACCGCGCCGCCGAA

AGAAAAAGAAGATCCGCTGAACAAATATACCTTTTGGGAAGTGAACCTGAA

AGAAAAATTTAGCGCGGATCTGGATCAGTTTCCGCTGGGCCGTAAATTTCT

GCTGCAGAGCGGCCTGAAAGCG"
```

Expression and Purification of Recombinant L1 Protein

Expression plasmid (HPV16-p3) containing the HPV16-L1 gene was transformed into *E. coli* strain HMS174 (DE3). The culture was grown at 37° C. in a bioreactor to an O.D. of 50. The culture was then induced with addition of 1 mM IPTG and the temperature lowered to 22° C. for 4 hours. The bacterial cells were then pelleted by centrifugation and stored at −70° C. until use. Cell pellets were resuspended in Homogenizing Buffer (200 ml/5 g cells; 200 mM NaCl, 50 mM Tris pH 8.0, 1 mM EDTA, 1 mM PMSF, 10% glycerol, 5 mM DTT, 2 protease inhibitor tablets (Roche)) with stirring on ice. Cells were lysed by passing through a Niro Panda (GEA Process Engineering, Columbia, Md.) homogenizer two times (2×) at 800-1000 bar at 4° C. The Panda-lysed homogenate was centrifuged at 22,000×g for 30 minutes at 4° C.

Clarified homogenate was loaded onto a Q Fast Flow (QFF) (GE Healthcare, Piscataway, N.J.) column equilibrated with 50 mM Tris, 200 mM NaCl, pH 8.1, 10% glycerol, 0.01% Tween 80 and 5 mM DTT. The QFF flow-through was precipitated with addition of solid ammonium sulfate to reach 30% saturation. The HPV16-L1 ammonium sulfate precipitate was resolubilized using the Panda and the soluble material after centrifugation was used for further purification (ASp). The ASp resolubilized sample was then adjusted to a conductivity of ~5 mS/cm at pH 8.5 and loaded onto a Q High Performance (QHP) column (GE Healthcare, Piscataway, N.J.). QHP fractions containing the L1 protein were pooled and quantitated for protein concentration. The protein was eluted with a linear salt gradient. SDS-PAGE analysis showed that the HPV L1 (52 kDa band) eluted as a major symmetrical peak. QHP pooled fractions containing purified HPV L1 were pooled and flash frozen in liquid $N_2$ until further use.

In one exemplary method, in order to examine the expression and solubility of L1 in *E. coli*, a series of deletions were made in the DNA expression plasmid at the 5'-end of the HPV16 L1 or HPV18L1 genes. These genes also were deleted in the C-terminal 29 amino acids. Cultures of *E. coli* containing the various expression constructs were grown in 250 ml liquid media at 37° C. to an OD595 of 4.0. Protein expression was induced by the addition of IPTG to each culture. The cultures were then incubated at 25° C. until an OD595 of 8.0 was achieved. The cultures were then centrifuged and the bacterial pellets were stored at −20° C.

The pellets were then resuspended in 100 ml buffer L and lysed by 2 passages through a Panda homogenizer at 800-1000 barr. A sample of each homogenate (whole cell lysate, WCL) was taken for SDS-PAGE analysis. The lysates were then clarified by centrifugation. The supernatants were removed and a sample (S1) of each was taken for SDS-PAGE analysis. The pellets were resuspended in equal volumes of water and a sample (P1) of each was taken for SDS-PAGE analysis. A sample of each supernatant was also precipitated with ammonium sulfate. Ammonium sulfate was added to a sample of each supernatant (0.164 g/ml) and rocked for 2 hours at 4° C. The ammonium sulfate solutions were then centrifuged at 13,000 g for 30 min. at 4° C. The supernatants were discarded and the precipitates were resuspended in an equal volume of buffer L. A sample (ASp) of each resuspended precipitate was taken for SDS-PAGE analysis.

Proteins with deletions or truncations of 5, 9 or 15 amino acids were expressed as illustrated (See for example FIGS. 7A-7C and FIG. 8) and were partially soluble. The protein with a deletion of 20 amino acids from the amino terminus was expressed as illustrated but had lower solubility than those with deletions of 5, 9 or 15 from the amino terminus above (See for example FIG. 9). Proteins with deletions of 3 or 25 amino acids were expressed poorly compared to the mutated proteins above (See for example FIGS. 7A-7C and FIG. 9). A deletion of 13 amino acids generated a protein that was expressed poorly when compared to the modified proteins above (FIG. 8). This may be due in part due to the presence of 2 prolines after the methionine at the amino-terminus. It is also possible that proteins with deletions of 3, 13 or 25 amino acids from the amino terminus were expressed at a high level but were unstable and were degraded.

TABLE 1

| | HPV16 L1 variants | | | | | | |
|---|---|---|---|---|---|---|---|
| | N3 | N5 | N9 | N13 | N15 | N20 | N25 |
| Expression | + | +++ | +++ | +/− | +++ | +++ | +/− |
| Soluble | + | + | + | + | + | +/− | + |

Deletions were also made in the DNA expression plasmid at the 5'-end of the HPV18 L1 gene. Proteins with deletions of 5, 9, 15 or 16 amino acids were expressed extremely well and were partially soluble (FIGS. 10A-10B and FIG. 11). Proteins having a deletion of about 5 amino acids appeared to have higher solubility compared to some other constructs. Deletions between 4 and 9 amino acids also appeared to have increased expression and solubility compared to some of the other truncated constructs.

TABLE 2

| HPV18 L1 variants | | | | |
|---|---|---|---|---|
| | N5 | N9 | N15 | N16 |
| Expression | +++ | +++ | +++ | ++ |
| Soluble | + | +/− | +/− | +/− |

All of the COMPOSITIONS and METHODS disclosed and claimed herein can be made and executed without undue experimentation in light of the present disclosure. While the compositions and methods have been described in terms of preferred embodiments, it is apparent to those of skill in the art that variations may be applied to the COMPOSITIONS and METHODS and in the steps or in the sequence of steps of the methods described herein without departing from the concept, spirit and scope herein. More specifically, certain agents that are both chemically and physiologically related may be substituted for the agents described herein while the same or similar results would be achieved. All such similar substitutes and modifications apparent to those skilled in the art are deemed to be within the spirit, scope and concept as defined by the appended claims.

What is claimed:

1. A bacterial plasmid construct comprising:
   a target Human Papilloma Virus (HPV) DNA molecule comprising a transcription start codon, wherein the target HPV DNA molecule encodes one or more proteins or peptides having at least 3 amino acids and no more than 24 amino acids deleted at the N-terminus, and up to 29 amino acids deleted at the C-terminus, the HPV DNA molecule comprising one or more of:
   1) the nucleic acid represented by SEQ ID NO: 1;
   2) the nucleic acid represented by SEQ ID NO: 2;
   3) the nucleic acid represented by SEQ ID NO: 3;
   4) the nucleic acid represented by SEQ ID NO: 4;
   5) the nucleic acid represented by SEQ ID NO: 5;
   6) the nucleic acid represented by SEQ ID NO: 6;
   7) the nucleic acid represented by SEQ ID NO: 7; or
   8) the nucleic acid represented by SEQ ID NO: 8;
   a promoter associated with the target HPV DNA molecule;
   a restriction site positioned between the promoter and the target HPV DNA molecule;
   a resistance gene capable of conferring resistance to a selection agent; and
   the plasmid construct is devoid of any tag, or tracking agent, making the construct tagless.

2. The bacterial plasmid construct of claim 1, wherein the target HPV DNA molecule encodes a single protein or a chimeric protein.

3. The bacterial plasmid construct of claim 1, wherein the target HPV DNA molecule encodes one or more proteins or peptides of use in an immunogenic composition against a target HPV.

4. The bacterial plasmid construct of claim 1, wherein the encoded molecule forms part of a capsomere.

5. The bacterial plasmid construct of claim 1, wherein the promoter is a Tac promoter.

6. A pharmaceutical composition comprising one or more proteins or peptides expressed from one or more bacterial constructs according to claim 1 and a pharmaceutically acceptable carrier.

7. The pharmaceutical composition according to claim 6, wherein the pharmaceutical composition is part of an immunogenic composition against one or more HPV type.

8. The pharmaceutical composition according to claim 7, wherein the pharmaceutical composition is part of an immunogenic composition against one or more HPV type selected from the group consisting of HPV16, HPV18, HPV31, HPV33, HPV35, HPV45, HPV52 and HPV58.

9. A method for eliciting an immune response to at least one HPV type in a subject, the method comprising administering to the subject a composition comprising the pharmaceutical composition of claim 6 and eliciting an immune response in the subject to the at least one HPV type.

10. A prophylactic method of treatment for eliciting an immune response to at least one HPV type in a subject comprising, administering to the subject, a prophylactically effective amount of a composition comprising the pharmaceutical composition of claim 6 and reducing or preventing infection to the at least one HPV type in the subject.

11. A therapeutic treatment method for eliciting an immune response to at least one HPV type infection in a subject comprising, administering to the subject a therapeutically effective amount of a pharmaceutical composition according to claim 6 and treating the HPV infection in the subject.

12. An isolated cell comprising the bacterial plasmid construct of claim 1.

13. An isolated preparation of expressed inclusion bodies comprising a polypeptide encoded by the bacterial plasmid construct of claim 1.

14. The bacterial plasmid construct of claim 1, wherein the plasmid bacterial construct is void of a GST tag.

15. The bacterial plasmid construct of claim 1, wherein the encoded proteins or peptides form a pentamer.

16. The bacterial plasmid construct of claim 1, wherein the bacterial plasmid construct does not encode a fusion protein or fusion peptide.

17. A kit comprising at least one of a bacterial plasmid construct and an encoded protein or peptide of the bacterial plasmid construct of claim 1 and at least one container.

18. The kit of claim 17, wherein the at least one of a bacterial construct and an encoded protein or peptide of the bacterial plasmid construct is in the form of a pharmaceutically acceptable composition further comprising a pharmaceutically acceptable carrier.

19. The bacterial plasmid construct of claim 1, wherein the target HPV DNA molecules encodes a truncated HPV protein or peptide of 3, 5, 9, 13, 15, 16, or 20 amino acids deleted at the N-terminus of the encoded protein or peptide.

20. The bacterial plasmid construct of claim 1, wherein the HPV DNA molecule encodes a truncated HPV protein or peptide with 3 amino acids deleted at the N-terminus and up to 29 amino acids deleted at the C-terminus.

21. The bacterial plasmid construct of claim 1, wherein the HPV DNA molecule encodes a truncated HPV protein or peptide with 29 amino acids deleted at the C-terminus.

* * * * *

SEQUENCE LISTING

<160> NUMBER OF SEQ ID NOS: 15

<210> SEQ ID NO 1
<211> LENGTH: 1401
<212> TYPE: DNA
<213> ORGANISM: Human papillomavirus type 16

<400> SEQUENCE: 1

```
accgtgtatc tgccgccggt gcctgtgagc aaagttgtga gcaccgatga atatgtggcg      60
cgtaccaaca tttattatca tgcgggcacc agccgtctgc tggcggtggg ccatccgtat     120
tttccgatca agaaaccgaa caacaacaaa attctggtgc cgaaagtgag cggcctgcag     180
tatcgtgtgt ttcgtattca tctgcctgat ccaaacaaat ttggctttcc ggataccagc     240
ttttataacc cggatacccca gcgtctggtg tgggcatgcg tgggtgtgga agtgggtcgt     300
ggtcagccgc tgggtgtggg cattagcggc catccgctgc tgaacaaact ggatgatacc     360
gaaaacgcga gcgcgtatgc ggcgaacgcg ggcgtggata ccgtgaatg cattagcatg     420
gattataaac agacccagct gtgcctgatt ggctgcaaac cgccgattgg cgaacattgg     480
ggtaaaggca gcccgtgcac caacgtggca gtgaacccgg gtgattgccc gccgctggaa     540
ctgattaaca ccgtgattca ggatggcgat atggtggata ccggctttgg cgcgatggat     600
tttaccaccc tgcaggcgaa caaaagcgaa gtgccgctgg atatttgcac cagcatttgc     660
aaatatccgg attatattaa aatggttagc gaaccgtatg gcgatagcct gtttttctac     720
ctgcgtcgtg aacagatgtt tgtgcgtcat ctgtttaacc gtgcgggcgc ggtgggcgaa     780
aacgtgccgg atgatctgta tattaaaggc agcggcagca ccgcgaacct ggcgagcagc     840
aactattttc cgaccccgag cggcagcatg gtgaccagcg atgcgcagat ttttaacaaa     900
ccgtattggc tgcagcgtgc gcagggccat aacaacggca tttgctgggg caaccagctg     960
tttgtgaccg tggtggatac cacccgtagc accaacatga gcctgtgcgc ggcgattagc    1020
accagcgaaa ccacctataa aaacaccaac tttaaagaat atctgcgtca tggcgaagaa    1080
tatgatctgc agtttatttt tcagctgtgc aaaattaccc tgaccgcgga tgtgatgacc    1140
tatattcata gcatgaacag caccattctg gaagattgga ctttggcct gcagccgccg    1200
ccgggcggca ccctggaaga tacctatcgt tttgtgacca gccaggcgat tgcgtgccag    1260
aaacataccc cgccggcgcc gaaagaagat ccgctgaaaa aatataccct tgggaagtg    1320
aacctgaaag aaaaatttag cgcggatctg gatcagtttc cgctgggccg taaatttctg    1380
ctgcaggcgg gcctgaaagc g                                             1401
```

<210> SEQ ID NO 2
<211> LENGTH: 1404
<212> TYPE: DNA
<213> ORGANISM: Human papillomavirus type 18

<400> SEQUENCE: 2

```
accgtgtatc tgccgccgcc gagcgtggcg cgtgtggtga acaccgatga ttatgtgacc      60
cgcaccagca tcttctacca tgcgggcagc agccgtctgc tgaccgtggg caacccgtat     120
tttcgtgtgc cggcaggtgg aggcaacaaa caggatattc cgaaagtgag cgcgtatcag     180
tatcgtgtgt tcgtgtgca gctgcctgat ccaaacaaat ttggcctgcc ggataccagc     240
atttataacc cggaaaccca cgtctggtg tgggcatgcg ccggtgtgga aattggtcgt     300
ggtcagccgc tgggtgtggg tctgagcggt catccgtttt ataacaaact ggatgatacc     360
gaaagcagcc atgcggcgac cagcaacgtg agcgaagatg tgcgtgataa cgtgagcgtg     420
gattataaac agacccagct gtgcattctg gctgcgcgc cggcgattgg cgaacattgg     480
gcaaaaggta ccgcatgcaa aagcgtccg ctgagccagg gcgattgccc gccgctggaa     540
ctgaaaaaca ccgtgctgga agatggcgat atggtggata ccggctatgg cgcgatggat     600
tttagcaccc tgcaggatac caaatgcgaa gtgccgctgg atatttgcca gagcatttgc     660
aaatatccgg attatctgca gatgagcgca gatccatatg gcgatagcat gtttttctgc     720
ctgcgtcgtg aacagctgtt tgcgcgtcat ttttggaacc gtgcgggcac catgggcgat     780
accgtgccgc agagcctgta tattaaaggt accggtatgc gcgcaagccc gggcagctgc     840
gtgtatagcc cgagcccgag cggcagcatt gtgaccagcg atagccagct gtttaacaaa     900
ccgtattggc tgcataaagc gcagggccat aacaacggcg tgtgctggca taaccagctg     960
tttgtgaccg tggtggatac caccccgcagc accaacctga ccatttgcgc gagcacccag    1020
agcccggtgc cgggccagta tgatgcgacc aaatttaaac agtatagccg tcatgtggaa    1080
gaatatgatc tgcagtttat ttttcagctg tgcaccatta ccctgaccgc ggatgtgatg    1140
agctatattc atagcatgaa cagcagcatt ctggaagatt ggaactttgg cgtgccgccg    1200
ccgccgacca ccagcctggt ggataccat cgtttttgtgc agagcgtggc gattacctgc    1260
cagaaagatg cggcgccggc ggaaaacaaa gatccgtacg ataaactgaa attctggaac    1320
gtggatctga agaaaaaatt cagcctggat ctggatcagt atccgctggg ccgtaaattt    1380
ctggtgcagg cgggcctgcg tcgt                                          1404
```

<210> SEQ ID NO 3
<211> LENGTH: 1404
<212> TYPE: DNA
<213> ORGANISM: Human papillomavirus type 31

<400> SEQUENCE: 3

```
accgtgtatc tgccgccggt gcctgtgagc aaagttgtga gcaccgatga atatgtgacc      60
cgtaccaaca tttattatca tgcgggcagc gcgcgtctgc tgaccgtggg ccatccgtat     120
tatagcattc cgaaaagcga taacccaaag aaaatcgtgg tgccgaaagt gagcggcctg     180
cagtatcgtg tgtttcgtgt gcgtctgcct gatccaaaca aatttggctt ccgataccc    240
agctttttata acccggaaac ccagcgtctg gtgtgggcat gcgtgggtct ggaagtgggt     300
cgtggtcagc cgctgggtgt gggcattagc ggccatccgc tgctgaacaa atttgatgat     360
accgaaaaca gcaaccgtta tgcaggtgga ccgggcaccg ataaccgtga atgcattagc     420
atggattata acagacccca gctgtgcctg ctgggctgca aaccgccgat tggcgaacat     480
tggggcaaag cgagcccgtg cagcaacaac gcgattaccc cgggcgattg cccgccgctg     540
gaactgaaaa acagcgtgat tcaggatggc gatatggtgg ataccggctt tggcgcgatg    600
```

```
gattttaccg cgctgcagga taccaaaagc aacgtgccgc tggatatttg caacagcatt      660
tgcaaatatc cggattatct gaaaatggtg gcggaaccgt atggcgatac cctgtttttc      720
tacctgcgtc gtgaacagat gtttgtgcgt catttcttta accgtagcgg caccgtgggc      780
gaaagcgtgc cgaccgatct gtatattaaa ggcagcggca gcaccgcgac cctggcgaac      840 agcaccctatt ttccgacccc gagcggcagc atggtgacca gcgatgcgca gattttttaac      900 aaaccgtatt ggatgcagcg tgcgcagggc cataacaacg gcatttgctg ggcaaccag       960 ctgtttgtga ccgtggtgga taccacccgt agcaccaaca tgagcgtgtg cgcggcgatt     1020
gcgaacagcg ataccacctt taaaagcagc aactttaaag aatatctgcg tcatggcgaa     1080
gaatttgatc tgcagtttat ttttcagctg tgcaaaatta ccctgagcgc ggatattatg     1140
acctatattc atagcatgaa cccggcgatt ctggaagatt ggaactttgg cctgaccacc     1200
ccgccgagcg gcagcctgga agataccctat cgttttgtga ccagccaggc gattacctgc     1260
cagaaaaccg cgccgcagaa accgaaagaa gatccgttta agattatgt gttttgggaa     1320 gtgaacctga agaaaaaatt tagcgcggat ctggatcagt ttccgctggg ccgtaaattt     1380
ctgctgcagg cgggctatcg tgcg                                            1404

<210> SEQ ID NO 4
<211> LENGTH: 1398
<212> TYPE: DNA
<213> ORGANISM: Human papillomavirus type 33

<400> SEQUENCE: 4
accgtgtatc tgccgccggt gcctgtgagc aaagttgtga gcaccgatga atatgtgagc       60
cgtaccagca tttattatta tgcgggcagc agccgtctgc tggcggtggg ccatccgtat      120
tttagcatta aaaacccgac caacgcgaaa aaactgctgg tgccgaaagt gagcggcctg      180
cagtatcgtg tgtttcgtgt gcgtctgcct gatccaaaca aatttggctt ccggatacc       240 agcttttata acccggatac ccagcgtctg gtgtgggcat cgtgggtct ggaaattggt       300 cgtggtcagc cgctgggtgt gggtattagc ggtcatccgc tgctgaacaa atttgatgat       360
accgaaaccg gcaacaaata tccgggccag ccgggcgcgg ataaccgtga atgcctgagc       420
atggattata acagacccca gctgtgcctg ctgggctgca aaccgccgac cggtgaacat       480
tggggtaaag gcgtggcatg caccaacgca gcaccggcaa cgattgcccc gccgctggaa       540
ctgattaaca ccattattga agatggcgat atggtggata ccggctttgg ctgcatggat       600
tttaaacccc tgcaggcgaa caaaagcgat gtgccgattg atatttgcgg cagcacctgc       660
aaatatccgg attatctgaa atgaccagc gaaccgtatg gcgatagctt gttctttttc       720
ctgcgtcgag aacagatgtt tgtgcgtcat ttctttaacc gtgcgggcac cctgggcgaa       780
gcggtgccgg atgatctgta tattaaaggc agcggcacca ccgcgagcat tcagagcagc      840 gcattttttcc cgacccccgag cggcagcatg gtgaccagcg aaagccagct gtttaacaaa      900
ccgtattggc tgcagcgtgc gcagggccat aacaacggca tttgctgggg caaccaggtg       960
tttgtgaccg tggtggatac cacccgtagc accaacatga ccctgtgcac ccaggtgacc      1020
agcgatagca cctacaaaaa cgaaaacttc aaagaataca tccgtcatgt ggaagaatac      1080
gatctgcagt tcgtgttca gctgtgcaaa gtgaccctga ccgcggaagt gatgacctat      1140
attcatgcga tgaacccgga tattctggaa gattggcagt ttggcctgac cccgccgccg      1200
agcgcgagcc tgcaggatac ctatcgtttt gtgaccagcc aggcgattac ctgccagaaa      1260
accgtgccgc cgaaagaaaa agaagatccg ctgggcaaat acccttttg ggaagtggat      1320
```

```
ctgaaagaaa aatttagcgc ggatctggat cagtttccgc tgggccgtaa atttctgctg   1380
caggcgggcc tgaaagcg                                                 1398

<210> SEQ ID NO 5
<211> LENGTH: 1395
<212> TYPE: DNA
<213> ORGANISM: Human papillomavirus type 35

<400> SEQUENCE: 5
accgtgtatc tgccgcctgt gagcgtgagc aaagttgtga gcaccgatga atatgtgacc    60
cgtaccaaca tttattatca tgcgggcagc agccgtctgc tggcggtggg ccatccgtat   120
tatgcgatca agaaacagga tagcaacaaa attgcggtgc cgaaagtgag cggcctgcag   180
tatcgtgtgt ttcgtgtgaa actgcctgat ccaaacaaat ttggctttcc ggataccagc   240
ttttatgatc cggcaagcca gcgtctggtg tgggcatgca ccggtgtgga agtgggtcgt   300
ggtcagccgc tgggcgtggg cattagcggc catccgctgc tgaacaaact ggatgatacc   360
gaaaacagca acaaatatgt gggcaacagc ggcaccgata accgtgaatg cattagcatg   420
gattataaac agacccagct gtgcctgatt ggctgccgtc cgccgattgg cgaacattgg   480
ggcaaaggca ccccgtgcaa cgcgaaccag gtgaaagcgg gcgaatgccc gccgctggaa   540
ctgctgaaca ccgtgctgca ggatggcgat atggtggata ccggctttgg cgcgatggat   600
tttaccaccc tgcaggcgaa caaaagcgat gtgccgctgg atatttgcag cagcatttgc   660
aaatatccgg attatctgaa aatggttagc gaaccgtatg gcgatatgct gttttttctac   720 ctgcgtcgtg aacagatgtt tgtgcgtcat ctgtttaacc gtgcgggcac cgtgggcgaa   780
accgtgccgg cggatctgta tattaaaggc accaccggca ccctgccgag caccagctat   840
tttccgaccc cgagcggcag catggtgacc agcgatgcgc agattttttaa caaaccgtat   900 tggctgcagc gtgcgcaggg ccataacaac ggcatttgct ggagcaacca gctgtttgtg   960
accgtggtgg ataccacccg tagcaccaac atgagcgtgt gcagcgcggt gtctagtagc  1020
gatagcacct ataaaaacga taactttaaa gaatatctgc gtcatggcga agaatatgat  1080 ctgcagtttta tttttcagct gtgcaaaatt accctgaccg cggatgtgat gacctatatt  1140
catagcatga cccgagcat tctggaagat tggaactttg gcctgacccc gccgccgagc  1200
ggcaccctgg aagatacccta tcgttatgtg accagccagg cggtgacctg ccagaaaccg  1260
agcgcgccga aaccgaaaga tgatccgctg aaaaactata ccttttggga agtggatctg  1320
aaagaaaaat ttagcgcgga tctggatcag tttccgctgg ccgtaaatt tctgctgcag  1380 gcgggcctga aagcg                                                   1395

<210> SEQ ID NO 6
<211> LENGTH: 1413
<212> TYPE: DNA
<213> ORGANISM: Human papillomavirus type 45

<400> SEQUENCE: 6
accgtgtatc tgccgccgcc gagcgtggcg cgtgtggtta gcaccgatga ttatgtgagc    60
cgtaccagca tcttctacca tgcgggcagc agccgtctgc tgaccgtggg caaccccgtat   120 tttcgtgtgg tgccgaacgg cgcgggcaac aaacaggcgg tgccgaaagt gagcgcgtat   180
cagtatcgtg tgtttcgtgt ggcgctgcct gatccaaaca atttggcct gccgatagc    240 accatttata acccggaaac ccagcgtctg gtgtgggcat gcgtgggtat ggaaattggt   300
```

-continued

```
cgtggtcagc cgctgggtat tggtctgagc ggtcatccgt tttataacaa actggatgat      360
accgaaagcg cgcatgcggc gaccgcggtg attacccagg atgtgcgtga taacgtgagc      420
gtggattata aacagaccca gctgtgcatt ctgggctgcg tgccggcgat tggcgaacat      480
tgggcaaaag gtaccctgtg caaaccggca cagctgcagc cgggtgattg cccgccgctg      540
gaactgaaaa acaccattat tgaagatggc gatatggtgg ataccggcta tggcgcgatg      600
gattttagca ccctgcagga taccaaatgc gaagtgccgc tggatatttg ccagagcatt      660
tgcaaatatc cggattatct gcagatgagc gcagatccat atggcgatag catgtttttc      720
tgcctgcgtc gtgaacagct gtttgcgcgt cattttttgga accgtgcggg cgtgatgggc      780
gataccgtgc cgaccgatct gtatattaaa ggcaccagcg cgaacatgcg tgaaaccccg      840
ggcagctgcg tgtatagccc gagcccgagc ggcagcatta ttaccagcga tagccagctg      900
tttaacaaac cgtattggct gcataaagcg cagggccata caacggcat ttgctggcat      960
aaccagctgt ttgtgaccgt ggtggatacc cccgtagca ccaacctgac cctgtgcgcg     1020
agcacccaga cccggtgcc gagcacctat gatccgacca aatttaaaca gtatagccgt     1080
catgtggaag aatatgatct gcagtttatt tttcagctgt gcaccattac cctgaccgcg     1140
gaagtgatga gctatattca tagcatgaac agcagcattc tggaaaactg aactttggc     1200
gtgccgccgc cgccgaccac cagcctggtg gataccctatc gttttgtgca gagcgtggcg     1260
gtgacctgcc agaaagatac cacccccgccg gaaaaacagg acccatatga taaactgaaa     1320
ttttggaccg tggatctgaa agaaaaattt agcagcgatc tggatcagta ccgctgggc      1380
cgtaaatttc tggtgcaggc aggtctgcgt cga                                  1413
```

<210> SEQ ID NO 7
<211> LENGTH: 1413
<212> TYPE: DNA
<213> ORGANISM: Human papillomavirus type 52

<400> SEQUENCE: 7

```
accgtgtatc tgccgccggt gcctgtgagc aaagttgtga gcaccgatga atatgtgagc       60
cgtaccagca tttattatta tgcgggcagc agccgtctgc tgaccgtggg ccatccgtat      120
tttagcatta aaaacaccag cagcggcaac ggcaaaaaag tgctggtgcc gaaagtgagc      180
ggcctgcagt atcgtgtgtt tcgtattaaa ctgcctgatc aaacaaatt tggctttccg      240
gataccagct tttataaccc ggaaacccag cgtctggtgt gggcatgcac cggtctggaa      300
attggtcgtg gtcagccgct gggtgtgggt attagcggtc atccgctgct gaacaaattt      360
gatgataccg aaaccagcaa caaatatgcg ggcaaaccgg gcattgataa ccgtgaatgc      420
ctgagcatgg attataaaca gacccagctg tgcattctgg gctgcaaacc gccgattggc      480
gaacattggg gcaaaggcac cccgtgcaac aacaacagcg gcaacccggg cgattgcccg      540
ccgctgcagc tgattaacag cgtgattcag gatggcgata tggtggatac cggctttggc      600
tgcatggatt taacacccct gcaggcgagc aaaagcgatg tgccgattga tatttgcagc      660
agcgtgtgca aatatccgga ttatctgcag atggcgagcg aaccgtatgg cgatagcttg      720
ttcttttttcc tgcgtcgaga acagatgttt gtgcgtcatt tctttaaccg tgcgggcacc      780
ctgggcgatc cggtgccggg cgatctgtat attcagggca gcaacagcgg caacaccgcg      840
accgtgcaga gcagcgcatt ttttcccgacc ccgagcggca gcatggtgac cagcgaaagc      900
cagctgttta caaaccgta ttggctgcag cgtgcgcagg ccataacaa cggcatttgc      960
tggggcaacc agctgtttgt gaccgtggtg gataccaccc gtagcaccaa catgaccctg     1020
```

```
tgcgcggaag tgaaaaaaga aagcacctat aaaaacgaaa actttaaaga atatctgcgt      1080
catggcgaag aatttgatct gcagtttatt tttcagctgt gcaaaattac cctgaccgcg      1140
gatgtgatga cctatattca taaaatggat gcgaccattc tggaagattg cagtttggc      1200 ctgaccccgc cgccgagcgc gagcctggaa gatacctatc gttttgtgac cagcaccgcg      1260
attacctgcc agaaaaacac cccgccgaaa ggcaagaag atccgctgaa agattatatg      1320
ttttgggaag tggatctgaa agaaaaattt agcgcggatc tggatcagtt ccgctgggc       1380 cgtaaatttc tgctgcaggc aggtctgcag gca                                   1413

<210> SEQ ID NO 8
<211> LENGTH: 1398
<212> TYPE: DNA
<213> ORGANISM: Human papillomavirus type 58

<400> SEQUENCE: 8
accgtgtatc tgccgccggt gcctgtgagc aaagttgtga gcaccgatga atatgtgagc        60
cgtaccagca tttattatta tgcgggcagc agccgtctgc tggcggtggg caacccgtat       120
tttagcatta aaagcccgaa caacaacaaa aaagtgctgg tgccgaaagt gagcggcctg       180
cagtatcgtg tgtttcgtgt gcgtctgcct gatccaaaca aatttggctt tccggatacc       240
agcttttata acccggatac ccagcgtctg gtgtgggcat gcgtgggtct ggaaattggt       300
cgtggtcagc cgctgggtgt gggtgtgagc ggtcatccgt atctgaacaa atttgatgat       360
accgaaacca gcaaccgtta tccggcgcag ccgggcagcg ataaccgtga atgcctgagc       420
atggattata aacagaccca gctgtgcctg attggctgca aaccgccgac cggcgaacat       480
tggggcaaag cgtggcgtg caacaacaac gcggcggcga ccgattgccc gccgctggaa       540
ctgtttaaca gcattattga agatggcgat atggtggata ccggctttgg ctgcatggat       600
tttggcaccc tgcaggcgaa caaaagcgat gtgccgattg atatttgcaa cagcacctgc       660
aaatatccgg attatctgaa aatggcgagc gaaccgtatg gcgatagctt gttctttttc       720
ctgcgtcgag aacagatgtt tgtgcgtcat ttctttaacc gtgcgggcaa actgggcgaa       780
gcggtgccgg atgatctgta tattaaaggc agcggcaaca ccgcggtgat tcagagcagc       840
gcatttttcc cgaccccgag cggcagcatt gtgaccagcg aaagccagct gtttaacaaa       900
ccgtattggc tgcagcgtgc gcagggccat aacaacggca tttgctgggg caaccagctg       960
tttgtgaccg tggtggatac cacccgtagc accaacatga ccctgtgcac cgaagtgacc      1020
aaagaaggca cctataaaa cgataacttt aagaatatg tgcgtcatgt ggaagaatat       1080
gatctgcagt ttgtgtttca gctgtgcaaa attaccctga ccgcggaaat tatgacctat      1140
attcatacca tggatagcaa cattctggaa gattggcagt ttggcctgac cccgccgccg      1200
agcgcgagcc tgcaggatac ctatcgtttt gtgaccagcc aggcgattac ctgccagaaa      1260
accgcgccgc cgaaagaaaa agaagatccg ctgaacaaat atacctttg ggaagtgaac       1320 ctgaaagaaa aatttagcgc ggatctggat cagtttccgc tgggccgtaa atttctgctg      1380
cagagcggcc tgaaagcg                                                    1398

<210> SEQ ID NO 9
<211> LENGTH: 29
<212> TYPE: DNA
<213> ORGANISM: Artificial Sequence
<220> FEATURE:
<223> OTHER INFORMATION: Derived from Human Papilloma Virus DNA
```

```
<400> SEQUENCE: 9
agtagtcata tgaccgtgta tctgccgcc                                         29

<210> SEQ ID NO 10
<211> LENGTH: 30
<212> TYPE: DNA
<213> ORGANISM: Artificial Sequence
<220> FEATURE:
<223> OTHER INFORMATION: Derived from Human Papilloma Virus DNA

<400> SEQUENCE: 10
atctcgagtt attacgcttt caggcccgcc                                        30

<210> SEQ ID NO 11
<211> LENGTH: 30
<212> TYPE: DNA
<213> ORGANISM: Artificial Sequence
<220> FEATURE:
<223> OTHER INFORMATION: Derived from Human Papilloma Virus DNA

<400> SEQUENCE: 11
atctcgagtt attaacgacg caggcccgcc                                        30

<210> SEQ ID NO 12
<211> LENGTH: 30
<212> TYPE: DNA
<213> ORGANISM: Artificial Sequence
<220> FEATURE:
<223> OTHER INFORMATION: Derived from Human Papilloma Virus DNA

<400> SEQUENCE: 12
atctcgagtt attacgcacg atagcccgcc                                        30

<210> SEQ ID NO 13
<211> LENGTH: 30
<212> TYPE: DNA
<213> ORGANISM: Artificial Sequence
<220> FEATURE:
<223> OTHER INFORMATION: Derived from Human Papilloma Virus DNA

<400> SEQUENCE: 13
atctcgagtt attatcgacg cagacctgcc                                        30

<210> SEQ ID NO 14
<211> LENGTH: 30
<212> TYPE: DNA
<213> ORGANISM: Artificial Sequence
<220> FEATURE:
<223> OTHER INFORMATION: Derived from Human Papilloma Virus DNA

<400> SEQUENCE: 14
atctcgagtt attatgcctg cagacctgcc                                        30

<210> SEQ ID NO 15
<211> LENGTH: 30
<212> TYPE: DNA
<213> ORGANISM: Artificial Sequence
<220> FEATURE:
<223> OTHER INFORMATION: Derived from Human Papilloma Virus DNA

<400> SEQUENCE: 15
atctcgagtt attacgcttt caggccgctc                                        30
```